(12) United States Patent
Eriksson et al.

(10) Patent No.: US 7,388,020 B2
(45) Date of Patent: Jun. 17, 2008

(54) BENZIMIDAZOL DERIVATIVES MODULATE CHEMOKINE RECEPTORS

(75) Inventors: Tomas Eriksson, Lund (SE); Svetlana Ivanova, Lund (SE); Hans Lönn, Lund (SE)

(73) Assignee: AstraZeneca AB (SE)

( * ) Notice: Subject to any disclaimer, the term of this patent is extended or adjusted under 35 U.S.C. 154(b) by 168 days.

(21) Appl. No.: 10/472,412

(22) PCT Filed: Mar. 18, 2002

(86) PCT No.: PCT/SE02/00509

§ 371 (c)(1),
(2), (4) Date: Sep. 16, 2003

(87) PCT Pub. No.: WO02/074763

PCT Pub. Date: Sep. 26, 2002

(65) Prior Publication Data

US 2004/0116435 A1 Jun. 17, 2004

(30) Foreign Application Priority Data

Mar. 19, 2001 (SE) .................... 0100966
Aug. 22, 2001 (SE) .................... 0102807

(51) Int. Cl.
*A61K 31/445* (2006.01)
*C07D 401/04* (2006.01)

(52) U.S. Cl. .............. 514/322; 514/318; 514/321; 546/193; 546/197; 546/199

(58) Field of Classification Search ............ 514/318, 514/321, 322; 546/193, 197, 199
See application file for complete search history.

(56) References Cited

U.S. PATENT DOCUMENTS

| | | | |
|---|---|---|---|
| 3,203,992 A | 8/1965 | Kunz et al. | |
| 3,577,432 A | 5/1971 | Helsley et al. | |
| 3,755,584 A | 8/1973 | Plotnikoff et al. | |
| 3,818,017 A | 6/1974 | Janssen et al. | |
| 3,894,030 A | 7/1975 | Janssen et al. | |
| 4,029,801 A | 6/1977 | Cavalla et al. | |
| 4,080,328 A * | 3/1978 | Maruyama et al. | 546/199 |
| 4,166,119 A | 8/1979 | Effland et al. | |
| 4,264,613 A | 4/1981 | Regnier et al. | |
| 4,304,915 A * | 12/1981 | Berthold | 546/201 |
| 4,338,323 A | 7/1982 | Regnier et al. | |
| 5,576,321 A | 11/1996 | Krushinski, Jr. et al. | |
| 5,614,523 A | 3/1997 | Audia et al. | |
| 5,614,533 A | 3/1997 | Anderson et al. | |
| 5,627,196 A | 5/1997 | Audia et al. | |
| 5,741,789 A | 4/1998 | Hibschman et al. | |
| 5,789,402 A | 8/1998 | Audia et al. | |
| 6,911,458 B2 | 6/2005 | Eriksson et al. | 514/329 |
| 6,927,222 B2 | 8/2005 | Hansen et al. | 514/292 |
| 6,943,188 B2 | 9/2005 | Eriksson et al. | 514/424 |
| 6,951,874 B2 | 10/2005 | Hansen et al. | 514/323 |
| 7,005,439 B2 | 2/2006 | Eriksson et al. | 514/326 |
| 2005/0090494 A1 | 4/2005 | Eriksson et al. | 514/241 |
| 2005/0239801 A1 | 10/2005 | Eriksson et al. | 514/255.05 |

FOREIGN PATENT DOCUMENTS

| | | |
|---|---|---|
| DE | 37 23 568 | 1/1989 |
| DE | 37 23 648 | 1/1989 |
| DE | 197 03 131 | 7/1998 |
| DE | 197 55 268 | 6/1999 |
| EP | 0 095 454 | 11/1983 |
| EP | 0 128 007 | 12/1984 |
| EP | 0 496 691 | 7/1992 |
| EP | 0 587 311 | 3/1994 |
| EP | 0 722 941 | 7/1996 |
| EP | 0 903 349 | 3/1999 |
| FR | 2 190 430 | 2/1974 |
| GB | 1368012 | 9/1974 |
| WO | WO 93/25528 | 12/1993 |
| WO | WO 97/23458 | 7/1997 |
| WO | WO 98/32442 | 7/1998 |
| WO | WO 99/25686 | 5/1999 |
| WO | WO 99/31092 | 6/1999 |
| WO | WO 99/65895 | 12/1999 |
| WO | WO 00/35449 | 6/2000 |
| WO | WO 00/35451 | 6/2000 |
| WO | WO 00/53600 | 9/2000 |
| WO | WO 00/58305 | 10/2000 |
| WO | WO 00/69820 | 11/2000 |
| WO | WO 01/14333 | 3/2001 |
| WO | WO 01/43744 | 6/2001 |

(Continued)

OTHER PUBLICATIONS

Berthold 3-aminopropoxyayl . . . CA 93:8015 (1980).*

(Continued)

*Primary Examiner*—Celia Chang
(74) *Attorney, Agent, or Firm*—Fish & Richardson P.C.

(57) ABSTRACT

The invention provides compounds of general formula (I) wherein A, X, m, $R^1$, N, $R^2$, $Z^1$, $Z^2$, Q, $R^3$, $R^4$, $R^5$, $R^6$, $R^7$, $R^8$, t and $R^{16}$ are as defined in the specification, processes for their preparation, pharmaceutical compositions containing them and their use in therapy (I)

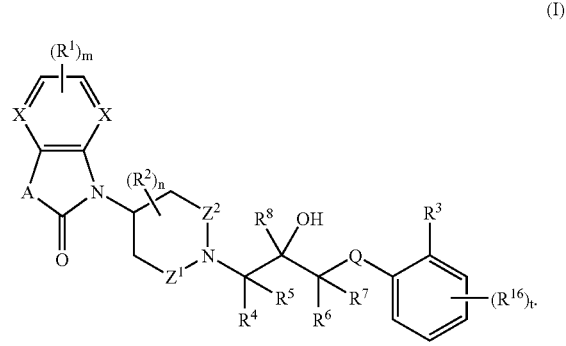

25 Claims, No Drawings

FOREIGN PATENT DOCUMENTS

| | | |
|---|---|---|
| WO | WO 01/44227 | 6/2001 |
| WO | WO 01/87839 | 11/2001 |

OTHER PUBLICATIONS

Tanabe et al. "Propanol . . . " CA 96:110143 (1982).*
Timmermans Hypotensive properties . . . CA 97:33112 (19820.*
Levine beta2 adrenergic mechanisms . . . CA 109:52680.*
Mizuhashi "A guinea pig model . . . " CA 122:71729 (1995).*
Chou et al. "Adrenergic regulation . . . " CA 129:3784 (1998).*
Wright et al. Subtype selective . . . CA 133:570800 (2000).*
Exhibit A CAS search result.*
Zenitz et al. "3-piperidino-loweralkyl indoles" CA 87:102164 (1977).*
Matsuo et al. "preparation of N-pentadienoylaminoalkyl . . . " CA 115:232091 (1991).*
Tanaka et al. "Antiallergic aeffects of novel compounds SWR-00151" CA 126:311929 (1997).*
Alcaraz et al. "Preparat of piperidinyl alcohols . . . " CA 139:197375 (2003).*
Bechtloff et al. "Pseudopolymorphs in industrial use" SciSearch 10289666 (2001).*
Black et al. "Increased chemical purity . . . " Scisearch 12765805 (2004).*
Hu et al. "Dependence of the chemical dynamics . . . " Beistein Abs. 5809171 (1993).*
Katritzky et al. "Heterocyclic Chemistry" Cambridge, p. 75 (1964).*
Saeki "molecular mechanism of reheumatoid . . . " CA 125:272100 (1996).*
Yamamoto :Espression of monocyte . . . CA 127:64176 (1997).*
Schmidt et al. "Immune mechanisms . . . " J. Allergy Clin, Immunol. April p. 673-682 (2000).*
Eriksson et al. "Preparation of benzimidazole . . . " CA 137:247698 (2002).*
U.S. Appl. No. 10/204,754, filed Aug. 23, 2002, Hansen et al.
U.S. Appl. No. 10/204,789, filed Aug. 23, 2002, Hansen et al.
U.S. Appl. No. 10/204,790, filed Aug. 23, 2002, Bodkin et al.
U.S. Appl. No. 10/311,667, filed Dec. 17, 2002, Eriksson et al.
U.S. Appl. No. 10/311,841, filed Dec. 17, 2002, Eriksson et al.
U.S. Appl. No. 10/468,179, filed Aug. 18, 2003, Brough et al.
U.S. Appl. No. 10/472,017, filed Sep. 19, 2003, Eriksson et al.
Archibald et al., "Antiinflammatory 4-acylaminopiperidines", *CAPLUS* 77:34355 (1972).
Cattanach et al., "Studies in the Indole Series. Part IV. Tetrahydro-1*H*-pyrido[4, 3-b]-indoles as Serotonin Antagonists", *J. Chem. Soc. C.* 10:1235-1243 (1968).
Cohen et al., "Cytokine function: A study in biologic diversity", *CAPLUS* 125:31527 (1996).
Friebe et al., "Piperidinopropyl derivatives and pharmaceutical compositions containing them", *CAPLUS* 94:103172 (1981).

Hesselgesser et al., "Identification and Characterization of Small Molecule Functional Antagonists of the CCR1 Chemokine Receptor", *J. Biol. Chem.* 273(25):15687-15692 (1998).
Howard et al., "Chemokines: progress toward identifying molecular targets for therapeutic agents", *Trends in Biotechnology* 14:46-51 (1996).
Manabu Hori Kim D. Janda, "A Soluble Polymer Approach to the "Fishing Out" Principle: Synthesis and Purification of β-Amino Alcohols", *J. Org. Chem.* 63:889-894 (1998).
Komai et al., "Structure-Activity Relationships of HIV-1 PR Inhibitors Containing AHPBA-II. Modification of Pyrrolidine Ring at P1' Proline", *Bioorganic & Medicinal Chemistry* 4(8):1365-1377 (1996).
Leclerc et al., "Derivatives Related to Betaxolol with I-and J-Adrenergic Activities", *Arzneim.-Forsch/Drug. Res.* 35(11):1357-1367 (1985).
Meurer et al., "Discovery of potent human CCR5 antagonists for the treatment of HIV-1 infection—II.", *CAPLUS* 2000:331722 (2000).
Navas III et al., "The Design and Synthesis of a Hapten for 1192U90, A Potential Atypical Antipsychotic Agent", *Synthetic Communications* 26(7):1411-1421 (1996).
Payard et al., "N-Aminomethylated Derivatives of Som eHydroxamic Acids as Anti-Inflammatories", *Eur. J. Med. Chem.* pp. 1-10 (1975).
Rubini et al., "Synthesis of Isosteric Methylene-Oxy Pseudodipeptide Analogues as Novel Amide Bond Surrogate Units", *Tetrahedron* 42(21):6039-6045 (1986).
STN Int'l, *CAPLUS* 1968.402884.
Timmermans et al., "Hypotensive Properties of Benzodioxane Derivatives Structurally Related to R 28935. Comparison to Activity with some Receptor Affinities", *Arch. int. Pharmacodyn.* 255:321-334 (1982).
Wright et al., "Discovery of Selective Dopamine D4 Receptor Antagonists: 1-Aryloxy-3-(4-Aryloxypiperidinyl)-2-Propanols", *Bioorganic & Medicinal Chemistry Letters* 7(11):1377-1380 (1997).
Eriksson et al., "Preparation of substituted 1-benzyl-4-piperidinamines as chemokine receptor modulators", *CAPLUS* 136:69740 (2001).
Hansen et al., "Preparation of substituted 1-phenoxy-3-pyrrolidino(or piperidino)propan-2-ols as chemokine receptor modulators", *CAPLUS* 135:195501 (2001).
Rollins, "Chemokines", *Blood* 90(3):909-928 (1997).
Barnes et al., "COPD: is there light at the end of the tunnel?", *Curr Opin Pharmacol* 4:263-272 (2004).
Barnes et al., "Prospects for new drugs for chronic obstructive pulmonary", *Lancet* 364:985-996 (2004).
de Boer, "Potential new drugs for therapy of chronic obstructive pulmonary disease", *Expert Opin. Investig. Drugs* 12:1067-1086 (2003).

* cited by examiner

BENZIMIDAZOL DERIVATIVES MODULATE CHEMOKINE RECEPTORS

The present invention relates to novel compounds, processes for their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C—X—C) and Cys-Cys (C—C) families. These are distinguished on the basis of a single amino acid insertion between the NH-proximal pair of cysteine residues and sequence similarity.

The C—X—C chemolines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MrP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those previously mentioned.

In accordance with the present invention, there is therefore provided a compound of general formula

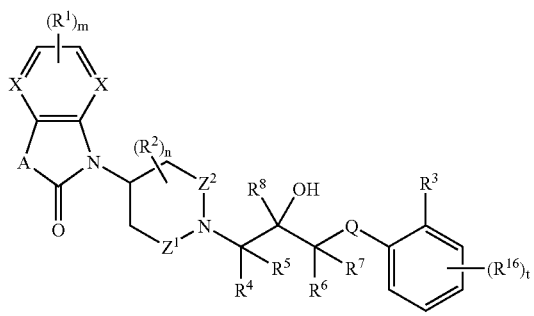

(I)

wherein

A represents an oxygen atom or a group NH;

each X independently represents a nitrogen atom or a group CH;

m is 0, 1, 2, 3 or 4;

each $R^1$ independently represents halogen, cyano, nitro, carboxyl, hydroxyl, $C_1$-$C_6$ alkyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^9R^{10}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido (—$SO_2NH_2$), $C_1$-$C_6$ alkylsulphonyl or —$C(O)NR^{11}R^{12}$;

n is 0, 1 or 2;

each $R^2$ independently represents a $C_1$-$C_6$ alkyl, $C_1$-$C_6$ alkoxycarbonyl, —$CH_2OH$ or carboxyl group;

$Z^1$ represents a bond or a group $(CH_2)_q$ where q is 1 or 2;

$Z^2$ represents a bond or a group $CH_2$, with the proviso that $Z^1$ and $Z^2$ do not both simultaneously represent a bond;

Q represents an oxygen or sulphur atom or a group $CH_2$ or NH;

$R^3$ represents —$NHC(O)R^{13}$, —$C(O)NR^{14}R^{15}$, —NH—$R^{15a}$ or —O—$R^{15b}$, or $R^3$ together with the six-membered ring to which it is attached forms a group of formula

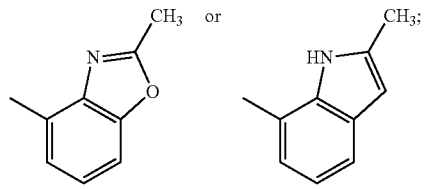

$R^4$, $R^5$, $R^6$ and $R^7$ each independently represent a hydrogen atom or a $C_1$-$C_6$ alkyl group, or $R^4$, $R^5$, $R^6$ and $R^7$ together represent a $C_1$-$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;

$R^8$ represents a hydrogen atom, a $C_1$-$C_6$ alkyl group or is linked to $R^4$ as defined above;

$R^9$ and $R^{10}$ each independently represent a hydrogen atom or a $C_1$-$C_6$ alkyl group, or $R^9$ and $R^{10}$ together with the nitrogen atom to which they are attached form a 4- to 7-membered saturated heterocycle;

$R^{11}$ and $R^{12}$ each independently represent a hydrogen atom or a $C_1$-$C_6$ alkyl group;

$R^{13}$ represents a group $C_1$-$C_6$ alkyl, $C_2$-$C_6$ alkenyl, $C_3$-$C_6$ cycloalkyl, adamantyl, $C_5$-$C_6$ cycloalkenyl, phenyl or a saturated or unsaturated 5- to 10-membered heterocyclic ring system comprising at least one ring heteroatom selected from nitrogen, oxygen and sulphur, each of which may be optionally substituted by one or more substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —$NHC(O)$—$R^{17}$;

$R^{14}$ and $R^{15}$ each independently represent (i) a hydrogen atom, (ii) a 3- to 6-membered saturated or unsaturated ring optionally comprising at least one ring heteroatom selected from nitrogen, oxygen and sulphur, the ring being optionally substituted with at least one substituent selected from hydroxyl, halogen, methyl, methoxy and trifluoromethyl, or (iii) a $C_1$-$C_6$ alkyl group optionally substituted by at least one substituent selected from halogen, trifluoromethyl, carboxyl, $C_1$-$C_6$ alkoxycarbonyl and a 5- to 6-membered saturated or unsaturated ring optionally comprising at least one ring heteroatom selected from nitrogen, oxygen and sulphur, the ring being optionally substituted with at least one substituent selected from halogen, methyl and trifluoromethyl, or R$^{14}$ and R$^{15}$ together with the nitrogen atom to which they are attached form a 4- to 7-membered saturated heterocycle;

R$^{15a}$ and R$^{15b}$ each independently represent a 5- to 6-membered saturated or unsaturated heterocyclic ring comprising at least one ring heteroatom selected from nitrogen, oxygen and sulphur, the ring being optionally substituted with at least one substituent selected from halogen, methyl and trifluoromethyl;

t is 0, 1, 2 or 3;

each R$^{16}$ independently represents halogen, cyano, nitro, carboxyl, hydroxyl, C$_3$-C$_6$ cycloalkyl, C$_1$-C$_6$ alkoxy, C$_1$-C$_6$ alkoxycarbonyl, C$_1$-C$_6$ haloalkyl, C$_1$-C$_6$ haloalkoxy, —NR$^{18}$R$^{19}$, C$_3$-C$_6$ cycloalkylamino, C$_1$-C$_6$ alkylthio, C$_1$-C$_6$ alkylcarbonyl, C$_1$-C$_6$ alkylcarbonylamino, sulphonamido (—SO$_2$NH$_2$), C$_1$-C$_6$ alkylsulphonyl, —C(O)NR$^{20}$R$^{21}$, —NR$^{22}$C(O)(NH)$_v$R$^{23}$, phenyl, or C$_1$-C$_6$ alkyl optionally substituted by at least one substituent selected from carboxyl and C$_1$-C$_6$ alkoxycarbonyl;

R$^{17}$ represents a C$_1$-C$_6$ alkyl, amino (—NH$_2$) or phenyl group;

R$^{18}$ and R$^{19}$ each independently represent a hydrogen atom or a C$_1$-C$_6$ alkyl group, or R$^{18}$ and R$^{19}$ together with the nitrogen atom to which they are attached form a 4- to 7-membered saturated heterocycle;

R$^{20}$ and R$^{21}$ each independently represent a hydrogen atom or a C$_1$-C$_6$ alkyl group optionally substituted by C$_1$-C$_6$ alkoxycarbonyl;

v is 0 or 1;

R$^{22}$ represents a hydrogen atom or a C$_1$-C$_6$ alkyl group; and

R$^{23}$ represents a hydrogen atom, or a C$_1$-C$_6$ alkyl group optionally substituted by at least one substituent selected from carboxyl, C$_1$-C$_6$ alkoxy and C$_1$-C$_6$ alkoxycarbonyl; or a pharmaceutically acceptable salt or solvate thereof.

In the context of the present specification, an alkyl or alkenyl substituent group or an alkyl moiety in a substituent group may be linear or branched. A haloalkyl or haloalkoxy substituent group will comprise at least one halogen atom, e.g. one, two, three or four halogen atoms. When R$^9$ and R$^{10}$ (or R$^{14}$ and R$^{15}$, or R$^{18}$ and R$^{19}$) represent a 4- to 7-membered saturated heterocycle, it should be understood that the only heteroatom present is the nitrogen atom to which R$^9$ and R$^{10}$ (or R$^{14}$ and R$^{15}$, or R$^{18}$ and R$^{19}$) are attached. In the definition of R$^{13}$, it should be noted that the saturated or unsaturated 5- to 10-membered heterocyclic ring system may have alicyclic or aromatic properties. Similarly, in the definition of R$^{14}$ and R$^{15}$, a 5- to 6-membered saturated or unsaturated ring optionally comprising at least one ring heteroatom may have alicyclic or aromatic properties. Similar comments apply in relation to R$^{15a}$ and R$^{15b}$. When R$^3$ together with the six-membered ring to which it is attached forms a group of formula

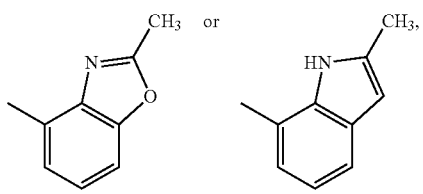

it will be understood that the six-membered ring may be substituted with the moiety (R$^{16}$)$_t$ in which t and R$^{16}$ are as defined above.

The integer m is preferably 0 or 1.

Each R$^1$ independently represents halogen (e.g. chlorine, fluorine, bromine or iodine), cyano, nitro, carboxyl, hydroxyl, C$_1$-C$_6$, preferably C$_1$-C$_4$, alkyl (e.g. methyl, ethyl, n-propyl, isopropyl, n-butyl, isobutyl, tert-butyl, n-pentyl or n-hexyl), C$_3$-C$_6$ cycloalkyl (cyclopropyl, cyclobutyl, cyclopentyl or cyclohexyl), C$_1$-C$_6$, preferably C$_1$-C$_4$, alkoxy (e.g. methoxy, ethoxy, n-propoxy or n-butoxy), C$_1$-C$_6$, preferably C$_1$-C$_4$, alkoxycarbonyl (e.g. methoxycarbonyl or ethoxycarbonyl), C$_1$-C$_6$, preferably C$_1$-C$_4$, haloalkyl (e.g. trifluoromethyl), C$_1$-C$_6$, preferably C$_1$-C$_4$, haloalkoxy (e.g. trifluoromethoxy), —NR$^9$R$^{10}$, C$_3$-C$_6$ cycloalkylamino (e.g. cyclopropylamino, cyclobutylamino, cyclopentylamino or cyclohexylamino), C$_1$-C$_6$, preferably C$_1$-C$_4$, alkylthio (e.g. methylthio or ethylthio), C$_1$-C$_6$, preferably C$_1$-C$_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), C$_1$-C$_6$, preferably C$_1$-C$_4$, alkylcarbonylamino (e.g. methylcarbonylamino or ethylcarbonylamino), sulphonamido, C$_1$-C$_6$, preferably C$_1$-C$_4$, alkylsulphonyl (e.g. methylsulphonyl, ethylsulphonyl, n-propylsulphonyl, isopropylsulphonyl, n-butylsulphonyl, n-pentylsulphonyl or n-hexylsulphonyl) or —C(O)NR$^{11}$R$^{12}$.

In an embodiment of the invention, each R$^1$ independently represents halogen or C$_1$-C$_6$ haloalkyl.

Each R$^2$ independently represents a C$_1$-C$_6$, preferably C$_1$-C$_4$, allyl (e.g. methyl, ethyl, n-propyl, isopropyl, n-butyl, isobutyl, tert-butyl, n-pentyl or n-hexyl), C$_1$-C$_6$, preferably C$_1$-C$_4$, alkoxycarbonyl (e.g. methoxycarbonyl or ethoxycarbonyl), —CH$_2$OH or carboxyl group. In an embodiment of the invention, n is 1 and R$^2$ represents a methyl, methoxycarbonyl, ethoxycarbonyl, —CH$_2$OH or carboxyl group.

In an embodiment of the invention, Z$^1$ and Z$^2$ both simultaneously represent CH$_2$.

In an embodiment of the invention, Q represents an oxygen atom.

R$^4$, R$^5$, R$^6$ and R$^7$ each independently represent a hydrogen atom or a C$_1$-C$_6$, preferably C$_1$-C$_4$, alkyl (e.g. methyl, ethyl, n-propyl, isopropyl, n-butyl, isobutyl, tert-butyl, n-pentyl or n-hexyl), or R$^4$, R$^5$, R$^6$ and R$^7$ together represent a C$_1$-C$_4$ alkylene chain linking the two carbon atoms to which they are attached to form a 4 to 7-membered saturated carbocycle (e.g. cyclopentyl or cyclohexyl), or R$^5$, R$^6$ and R$^7$ each represent a hydrogen atom and R$^4$ and R$^8$ together with the carbon atoms to which they are attached form a 5- to 6-membered saturated carbocycle (particularly cyclopentyl).

R$^8$ represents a hydrogen atom, a C$_1$-C$_6$, preferably C$_1$-C$_4$, alkyl group (e.g. methyl, ethyl, n-propyl, isopropyl, n-butyl, isobutyl, tert-butyl, n-pentyl or n-hexyl) or is linked to R$^4$ as defined above.

R$^9$ and R$^{10}$ each independently represent a hydrogen atom or a C$_1$-C$_6$, preferably C$_1$-C$_4$, alkyl group (e.g. methyl, ethyl, n-propyl, isopropyl, n-butyl, isobutyl, tert-butyl, n-pentyl or n-hexyl), or R$^9$ and R$^{10}$ together with the nitrogen atom to which they are attached form a 4- to 7-membered saturated heterocycle (e.g. pyrrolidinyl or piperidinyl).

R$^{11}$ and R$^{12}$ each independently represent a hydrogen atom or a C$_1$-C$_6$, preferably C$_1$-C$_4$, alkyl group (e.g. methyl, ethyl, n-propyl, isopropyl, n-butyl, isobutyl, tert-butyl, n-pentyl or n-hexyl).

R$^{13}$ represents a group C$_1$-C$_6$, preferably C$_1$-C$_5$, alkyl group (e.g. methyl, ethyl, n-propyl, isopropyl, n-butyl, isobutyl, tert-butyl, n-pentyl or n-hexyl), C$_2$-C$_6$, preferably $C_2$-$C_4$, alkenyl, $C_3$-$C_6$ cycloalkyl (cyclopropyl, cyclobutyl, cyclopentyl or cyclohexyl), adamantyl, $C_5$-$C_6$ cycloalkenyl, phenyl or a saturated or unsaturated 5- to 10-membered heterocyclic ring system comprising at least one ring heteroatom (e.g. one, two, three or four ring heteroatoms) selected from nitrogen, oxygen and sulphur, each of which (i.e. each of the recited groups and the ring system) may be optionally substituted by one or more (e.g. one, two, three or four) substituents independently selected from nitro, hydroxyl, oxo, halogen (e.g. fluorine, chlorine, bromine or iodine), carboxyl, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkylthio (e.g. methylthio or ethylthio), $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$-$C_6$, preferably $C_1$-$C_4$, alkoxycarbonyl (e.g. methoxycarbonyl or ethoxycarbonyl), phenyl and —NHC(O)—$R^{17}$.

The saturated or unsaturated 5- to 10-membered heterocyclic ring system may be monocyclic or polycyclic (e.g. bicyclic) and comprises up to four ring heteroatoms independently selected from nitrogen, oxygen and sulphur. Examples of ring systems that may be used include pyrrolidinyl, piperidinyl, pyrazolyl, thiazolidinyl, thienyl, isoxazolyl, thiadiazolyl, pyrrolyl, furanyl, thiazolyl, indolyl, quinolinyl, benzimidazolyl, triazolyl, tetrazolyl and pyridinyl.

In an embodiment of the invention, $R^{13}$ represents a group $C_1$-$C_6$ alkyl, phenyl or a saturated or unsaturated 5- to 6-membered heterocyclic ring system comprising at least one ring heteroatom (e.g. one or two ring heteroatoms independently) selected from nitrogen, oxygen and sulphur, each of which may be optionally substituted by one, two, three or four substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —NHC(O)—$R^{17}$.

In another embodiment of the invention, $R^{13}$ represents a group $C_1$-$C_6$ alkyl, phenyl or an unsaturated 5- to 6-membered heterocyclic ring system comprising at least one ring heteroatom (e.g. one or two ring heteroatoms independently) selected from nitrogen and oxygen, each of which may be optionally substituted by one or two substituents independently selected from halogen, $C_1$-$C_6$ alkyl and $C_1$-$C_6$ alkoxy.

$R^{14}$ and $R^{15}$ each independently represent (i) a hydrogen atom, (ii) a 3- to 6-membered saturated or unsaturated ring optionally comprising at least one ring heteroatom (e.g. one, two or three ring heteroatoms independently) selected from nitrogen, oxygen and sulphur (examples of rings include cyclopropyl, cyclobutyl, cyclopentyl, cyclohexyl, pyrolyl, imidazolyl, pyridinyl, pyrazinyl, pyridazinyl, pyrimidinyl, thienyl and furanyl), the ring being optionally substituted with at least one substituent (e.g. one, two or three substituents independently) selected from hydroxyl, halogen (e.g. fluorine, chlorine, bromine or iodine), methyl, methoxy and trifluoromethyl, or (iii) a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) optionally substituted by at least one substituent (e.g. one, two or three substituents independently) selected from halogen (e.g. fluorine, chlorine, bromine or iodine), trifluoromethyl, carboxyl, $C_1$-$C_6$, preferably $C_1$-$C_4$, alkoxycarbonyl and a 5- to 6-membered saturated or unsaturated ring optionally comprising at least one ring heteroatom (e.g. one, two or three ring heteroatoms independently) selected from nitrogen, oxygen and sulphur (examples of rings include cyclopentyl, cyclohexyl, pyrolyl, imidazolyl, pyridinyl, pyrazinyl, pyridazinyl, pyrimidinyl, thienyl and furanyl), the ring being optionally substituted with at least one substituent (e.g. one, two or three substituents independently) selected from halogen (e.g. fluorine, chlorine, bromine or iodine), methyl and trifluoromethyl, or $R^{14}$ and $R^{15}$ together with the nitrogen atom to which they are attached form a 4 to 7-membered saturated heterocycle (e.g. pyrrolidinyl or piperidinyl).

In an embodiment of the invention, $R^{14}$ and $R^{15}$ each independently represent (i) a hydrogen atom, (ii) a 3- to 6-membered saturated or unsaturated ring optionally comprising at least one ring heteroatom selected from nitrogen, oxygen and sulphur, the ring being optionally substituted with at least one substituent selected from halogen, methyl, methoxy and trifluoromethyl, or (iii) a $C_1$-$C_6$ alkyl group.

In another embodiment of the invention, $R^{14}$ and $R^{15}$ each independently represent (i) a hydrogen atom, (ii) cyclopropyl or pyridinyl, each of which may be optionally substituted with at least one substituent selected from halogen, methyl, methoxy and trifluoromethyl, or (iii) a $C_1$-$C_6$ alkyl group.

$R^{15a}$ and $R^{15b}$ each independently represent a 5- to 6-membered saturated or unsaturated heterocyclic ring comprising at least one ring heteroatom (e.g. one, two, three or four ring heteroatoms independently) selected from nitrogen, oxygen and sulphur, the ring being optionally substituted with at least one substituent (e.g. one, two or three substituents independently) selected from halogen (e.g. fluorine, chlorine, bromine or iodine), methyl and trifluoromethyl.

Each $R^{16}$ independently represents halogen (e.g. chlorine, fluorine, bromine or iodine), cyano, nitro, carboxyl, hydroxyl, $C_3$-$C_6$ cycloalkyl (cyclopropyl, cyclobutyl, cyclopentyl or cyclohexyl), $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkoxycarbonyl (e.g. methoxycarbonyl or ethoxycarbonyl), $C_1$-$C_6$, preferably $C_1$-$C_4$, haloalkyl (e.g. trifluoromethyl), $C_1$-$C_6$, preferably $C_1$-$C_4$, haloalkoxy (e.g. trifluoromethoxy), —$NR^{18}R^{19}$, $C_3$-$C_6$ cycloalkylamino (e.g. cyclopropylamino, cyclobutylamino, cyclopentylamino or cyclohexylamino), $C_1$-$C_6$, preferably $C_1$-$C_4$, alkylthio (e.g. methylthio or ethylthio), $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$-$C_6$, preferably $C_1$-$C_4$, alkylcarbonylamino (e.g. methylcarbonylamino or ethylcarbonylamino), sulphonamido, $C_1$-$C_6$, preferably $C_1$-$C_4$, alkylsulphonyl (e.g. methylsulphonyl, ethylsulphonyl, n-propylsulphonyl, isopropylsulphonyl, n-butylsulphonyl, n-pentylsulphonyl or n-hexylsulphonyl), —C(O)$NR^{20}R^{21}$, —$NR^{22}$C(O)—(NH)$_x R^{23}$, phenyl, or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) optionally substituted by at least one substituent (e.g. one, two or three substituents) independently selected from carboxyl and $C_1$-$C_6$, preferably $C_1$-$C_4$, alkoxycarbonyl (e.g. methoxycarbonyl or ethoxycarbonyl).

In an embodiment of the invention, each $R^{16}$ independently represents halogen, hydroxyl, cyano, $C_1$-$C_4$ alkoxy, $C_1$-$C_4$ alkoxycarbonyl, $C_1$-$C_4$ haloalkyl, $C_1$-$C_4$ alkylcarbonyl, phenyl or $C_1$-$C_4$ alkyl.

$R^{17}$ represents a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl), amino or phenyl group.

$R^{18}$ and $R^{19}$ each independently represent a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl), or $R^{18}$ and $R^{19}$ together with the nitrogen atom to which they are attached form a 4 to 7-membered saturated heterocycle (e.g. pyrrolidinyl or piperidinyl).

$R^{20}$ and $R^{21}$ each independently represent a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) optionally substituted by a $C_1$-$C_6$, preferably $C_1$-$C_4$, alkoxycarbonyl substituent group.

$R^{22}$ represents a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl).

$R^{23}$ represents a hydrogen atom, or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) optionally substituted by at least one substituent (e.g. one, two or three substituents independently) selected from carboxyl, $C_1$-$C_6$, preferably $C_1$-$C_4$, alkoxy or $C_1$-$C_6$, preferably $C_1$-$C_4$, alkoxycarbonyl.

In an embodiment of the invention,

A represents an oxygen atom or a group NH;
each X represents a group CH;
m is 0 or 1;
$R^1$ represents halogen or $C_1$-$C_6$ haloalkyl;
n is 0;
$Z^1$ represents $CH_2$;
$Z^2$ represents $CH_2$;
Q represents an oxygen atom;
$R^3$ represents —NHC(O)$R^{13}$ or —C(O)N$R^{14}R^{15}$, or
$R^3$ together with the six-membered ring to which it is attached forms a group of formula

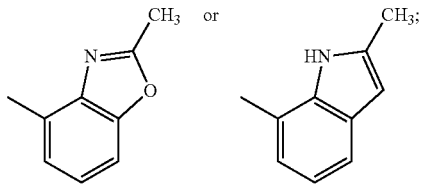

$R^4$, $R^5$, $R^6$ and $R^7$ each represent a hydrogen atom;
$R^8$ represents a hydrogen atom or a $C_1$-$C_6$ alkyl group;
$R^{13}$ represents a group $C_1$-$C_6$ alkyl, phenyl or an unsaturated 5- to 6-membered heterocyclic ring system comprising at least one ring heteroatom selected from nitrogen and oxygen, each of which may be optionally substituted by one or two substituents independently selected from halogen, $C_1$-$C_6$ alkyl and $C_1$-$C_6$ alkoxy;
$R^{14}$ and $R^{15}$ each independently represent (i) a hydrogen atom, (ii) cyclopropyl or pyridinyl, each of which may be optionally substituted with at least one substituent selected from halogen, methyl, methoxy and trifluoromethyl, or (iii) a $C_1$-$C_6$ alkyl group.
t is 0, 1 or 2; and
each $R^{16}$ independently represents halogen, hydroxyl or $C_1$-$C_6$ alkoxy.

Examples of compounds of the invention include:
N-(2-{2-Hydroxy-3-[4-(2-oxo-1,3-benzoxazol-3(2H)-yl)-1-piperidinyl]propoxy}phenyl)acetamide hydrochloride,
N-(2-{2-Hydroxy-2-methyl-3-[4-(2-oxo-2,3-dihydro-1H-benzimidazol-1-yl)-1-piperidinyl]propoxy}phenyl)-2-pyridinecarboxamide,
N-(2-{2-Hydroxy-3-[4-(2-oxo-2,3-dihydro-1H-benzimidazol-1-yl)-1-piperidinyl]propoxy}phenyl)benzamide hydrochloride,
2-{2-Hydroxy-3-[4-(2-oxo-2,3-dihydro-1H-benzimidazol-1-yl-1-piperidinyl]propoxy}-N-methylbenzamide,
N-[2-(2-Hydroxy-3-{4-[2-oxo-5-(trifluoromethyl)-2,3-dihydro-1H-benzimidazol-1-yl]-1-piperidinyl}propoxy)phenyl]acetamide,
N-(2-{3-[4-(6-Chloro-2-oxo-2,3-dihydro-1H-benzimidazol-1-yl)-1-piperidinyl]-2-hydroxypropoxy}phenyl)-4-methylbenzamide,
4-Chloro-N-[2-(2-hydroxy-3-{4-([2-oxo-5-(trifluoromethyl)-2,3-dihydro-1H-benzimidazol-1-yl]-1-piperidinyl}propoxy)phenyl]benzamide,
N-[2-({(2R)-3-[4-(5-Fluoro-2-oxo-2,3-dihydro-1H-benzimidazol-1-yl)-1-piperidinyl]-2-hydroxypropyl}oxy)phenyl]acetamide hydrochloride,
N-(2-{3-[4-(5-Fluoro-2-oxo-2,3-dihydro-1H-benzimidazol-1-yl)-1-piperidinyl]-2-hydroxypropoxy}phenyl)benzamide,
N-[2-({(2S)-3-[4-(5-Fluoro-2-oxo-2,3-dihydro-1H-benzimidazol-1-yl)-1-piperidinyl]-2-hydroxypropyl}oxy)phenyl]acetamide hydrochloride,
N-(2-{3-[4-(5-Fluoro-2-oxo-2,3-dihydro-1H-benzimidazol-1-yl)-1-piperidinyl]-2-hydroxypropoxy}phenyl)acetamide,
N-(2-{3-[4-(6-Chloro-2-oxo-2,3-dihydro-1H-benzimidazol-1-yl)-1-piperidinyl]-2-hydroxypropoxy}phenyl)acetamide,
N-(2-{3-[4-(5-Fluoro-2-oxo-2,3-dihydro-1H-benzimidazol-1-yl)-1-piperidinyl]-2-hydroxypropoxy}phenyl)-4-methoxybenzamide,
N-[2-(2-Hydroxy-3-{4-[2-oxo-5-(trifluoromethyl)-2,3-dihydro-1H-benzimidazol-1-yl[-1-piperidinyl}propoxy)phenyl]benzamide,
4-Chloro-N-(2-{3-[4-(6-chloro-2-oxo-2,3-dihydro-1H-benzimidazol-1-yl)-1-piperidinyl]-2-hydroxypropoxy}phenyl)benzamide,
N-(2-{2-Hydroxy-3-[4-(2-oxo-1,3-benzoxazol-3(2H)-yl)-1-piperidinyl]propoxy}phenyl)-4-methylbenzamide,
N-(2-{2-Hydroxy-2-methyl-3-[4-(2-oxo-2,3-dihydro-1H-benzimidazol-1-yl)-1-piperidinyl]propoxy}phenyl)acetamide,
4-Chloro-N-(2-{3-[4-(5-fluoro-2-oxo-2,3-dihydro-1H-benzimidazol-1-yl)-1-piperidinyl]-2-hydroxypropoxy}phenyl)benzamide,
N-(2-{2-Hydroxy-3-(4-(2-oxo-1,3-benzoxazol-3(2H)-yl)-1-piperidinyl]propoxy}phenyl)benzamide,
N-(2-{3-[4-(5-Fluoro-2-oxo-2,3-dihydro-1H-benzimidazol-1-yl)-1-piperidinyl]-2-hydroxypropoxy}phenyl)-4-methylbenzamide,
N-(2-{2-Hydroxy-3-[4-(2-oxo-2,3-dihydro-1H-benzimidazol-1-yl)-1-piperidinyl]propoxy}phenyl)acetamide hydrochloride,
4-Chloro-N-(2-{2-hydroxy-3-[4-(2-oxo-1,3-benzoxazol-3-(2H)-yl)-1-piperidinyl]propoxy}phenyl)benzamide,
4-Chloro-N-(2-{2-hydroxy-3-[4-(2-oxo-2,3-dihydro-1H-benzimidazol-1-yl)-1-piperidinyl]propoxy}phenyl)benzamide, N-(2-{2-Hydroxy-2-methyl-3-[4-(2-oxo-2,3-dihydro-1H-benzimidazol-1-yl)-1-piperidinyl]propoxy}phenyl)benzamide, N-(2-{3-[4-(5-Fluoro-2-oxo-2,3-dihydro-1H-benzimidazol-1-yl)-1-piperidinyl]-2-hydroxypropoxy}phenyl)-5-isoxazolecarboxamide, N-(2-{2-Hydroxy-3-[4-(2-oxo-1,3-benzoxazol-3(2H)-yl)-1-piperidinyl]propoxy}phenyl)acetamide, N-(2-{2-Hydroxy-3-[4-(2-oxo-2,3-dihydro-1H-benzimidazol-1-yl)-1-piperidinyl]propoxy}phenyl)acetamide, N-(2-{2-Hydroxy-3-[4-(2-oxo-2,3-dihydro-1H-benzimidazol-1-yl)-1-piperidinyl]propoxy}phenyl)-4-methylbenzamide, 2-{3-[4-(5-Fluoro-2-oxo-2,3-dihydro-1H-benzimidazol-1-yl)-1-piperidinyl]-2-hydroxypropoxy}-N-methylbenzamide, N-[4-Fluoro-2-({(2S)-3-[4-(5-fluoro-2-oxo-2,3-dihydro-1H-benzimidazol-1-yl)-1-piperidinyl]-2-hydroxypropyl}oxy)phenyl]acetamide trifluoroacetate, 5-Fluoro-1-(1-{(2S)-2-hydroxy-3-[(2-methyl-1,3-benzoxazol-4-yl)oxy]propyl)}-4-piperidinyl)-1,3-dihydro-2H-benzimidazol-2-one trifluoroacetate, N-[2-({(2S)-3-[4-(5-Fluoro-2-oxo-2,3-dihydro-1H-benzimidazol-1-yl)-1-piperidinyl]-2-hydroxypropyl}oxy)-4-methoxyphenyl]acetamide, 2-{3-[4-(5-Fluoro-2-oxo-2,3-dihydro-benzoimidazol-1-yl)piperidin-1-yl]-2-hydroxy-propoxy}-N-cyclopropyl-benzamide, 2-{3-[4-(5-Fluoro-2-oxo-2,3-dihydro-benzoimidazol-1-yl)piperidin-1-yl]-2-hydroxy-propoxy}-N-3-hydroxypyridin-2-yl)-benzamide, N-[2-({(2S)-3-[4-(5-Chloro-2-oxo-2,3-dihydro-1H-benzimidazol-1-yl)-1-piperidinyl]-2-hydroxypropyl}oxy)phenyl]acetamide(trifluoroacetate), 2-({(2S)-3-[4-(5-Chloro-2-oxo-2,3-dihydro-1H-benzimidazol-1-yl)-1-piperidinyl]-2-hydroxypropyl}-N-cyclopropylbenzamide(trifluoroacetate), N-2-{3-[4-(5-Chloro-2-oxo-2,3-dihydro-benzoimidazol-1-yl)piperidin-1-yl]-2-hydroxy-propoxy}-4-fluorophenyl)-acetamide, N-(5-Chloro-2-{3-[4-(5-fluoro-2-oxo-2,3-dihydro-benzoimidazol-1-yl)piperidin-1-yl]-2-hydroxy-propoxy}-phenyl)-acetamide, 5-Fluoro-1-(1-{(2S)-2-hydroxy-3-[(2-methyl-1H-indol-7-yl)oxy]propyl}-4-piperidinyl)-1,3-dihydro-2H-benzimidazol-2-one, 5-Fluoro-1-(1-{(2S)-2-hydroxy-3-[(6-methoxy-2-methyl-1,3-benzoxazol-4-yl)oxy]propyl}4-piperidinyl)-1,3-dihydro-2H-benzimidazol-2-one trifluoroacetate, 5-Fluoro-1-(1-{(2S)-2-hydroxy-3-[(6-hydroxy-2-methyl-1,3-benzoxazol-4-yl)oxy]propyl}-4-piperidinyl)-1,3-dihydro-2H-benzimidazol-2-one trifluoroacetate, N-[5-Bromo-2-({(2S)-3-[4-(5-fluoro-2-oxo-2,3-dihydro-1H-benzimidazol-1-yl)-1-piperidinyl]-2-hydroxypropyl}oxy)-4-methoxyphenyl]acetamide, N-Cyclopropyl-4-fluoro-2-({(2S)-3-[4-(5-fluoro-2-oxo-2,3-dihydro-1H-benzimidazol-1-yl)-1-piperidinyl]-2-hydroxypropyl}oxy)benzamide trifluoroaceate, N-[2-({(2S)-3-[4-(5-Fluoro-2-oxo-2,3-dihydro-1H-benzimidazol-1-yl)-1-piperidinyl]-2-hydroxypropyl}oxy)-4-hydroxyphenyl]acetamide, N-[5-Bromo-2-({(2S)-3-[4-(5-fluoro-2-oxo-2,3-dihydro-1H-benzimidazol-1-yl)-1-piperidinyl]-2-hydroxypropyl}oxy)-4-hydroxyphenyl]acetamide, N-[4,5-Difluoro-2-({(2S)-3-[4-(5-fluoro-2-oxo-2,3-dihydro-1H-benzimidazol-1-yl)-1-piperidinyl]-2-hydroxypropyl}oxy)phenyl]acetamide, and N-[5-Fluoro-2-({(2S)-3-[4-(5-fluoro-2-oxo-2,3-dihydro-1H-benzimidazol-1-yl)-1-piperidinyl]-2-hydroxypropyl}oxy)phenyl]acetamide.

The present invention further provides a process for the preparation of a compound of formula (I) as defined above which comprises, (a) reacting a compound of general formula

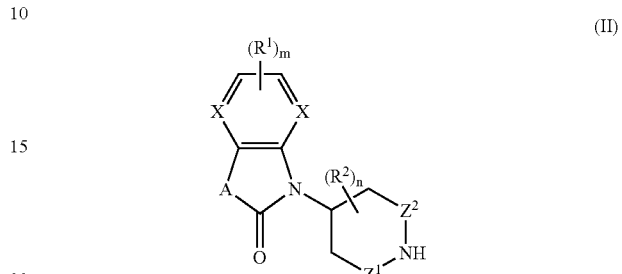

(II)

wherein A, X, m, $R^1$, n, $R^2$, $Z^1$ and $Z^2$ are as defined in formula (I), with a compound of general formula

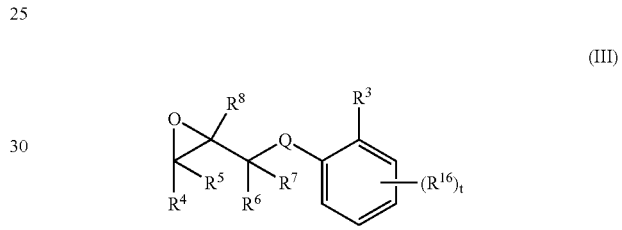

(III)

wherein Q, $R^3$, $R^4$, $R^5$, $R^6$, $R^7$, $R^8$, t and $R^{16}$ are as defined in formula (I); or (b) reacting a compound of general formula

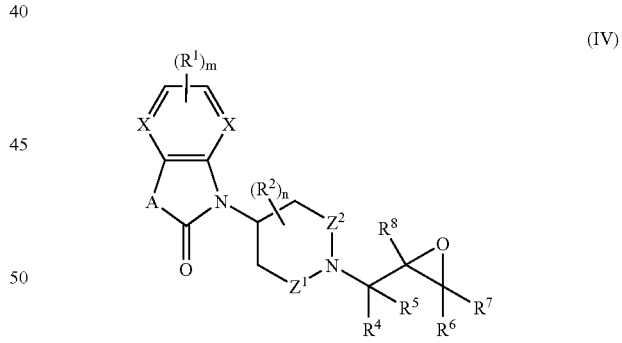

(IV)

wherein A, X, m, $R^1$, n, $R^2$, $Z^1$, $Z^2$, $R^4$, $R^5$, $R^6$, $R^7$ and $R^8$ are as defined in formula (I), with a compound of general formula

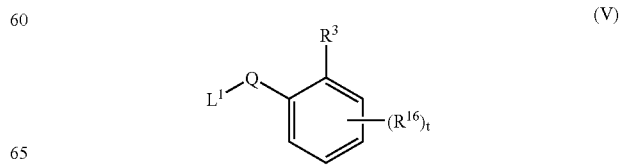

(V)

wherein $L^1$ represents a hydrogen atom or an activating group (e.g. Li when Q is $CH_2$) and Q, $R^3$, t and $R^{16}$ are as defined in formula (I); or (c) when $R^3$ represents $-NHC(O)R^{13}$, reacting a compound of general formula (VI)

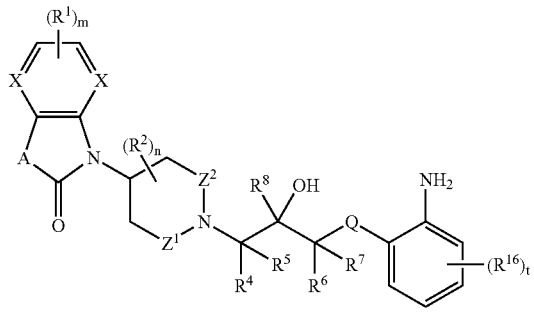

wherein A, X, m, $R^1$, n, $R^2$, $Z^1$, $Z^2$, $R^4$, $R^5$, $R^6$, $R^7$, $R^8$, Q, t and $R^{16}$ are as defined in formula (I), with a compound of general formula (VII)

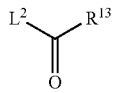

wherein $L^2$ represents a leaving group (e.g. a hydroxyl group or a halogen atom such as chlorine) and $R^{13}$ is as defined in formula (I); or (d) when $R^3$ represents $-C(O)NR^{14}R^{15}$, reacting a compound of general formula (VIII)

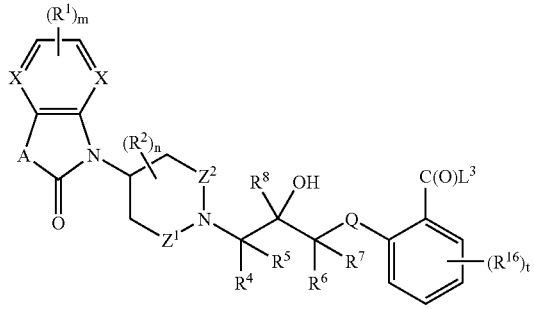

wherein $L^3$ represents a leaving group (e.g. a hydroxyl group or a halogen atom such as chlorine) and A, X, m, $R^1$, n, $R^2$, $Z^1$, $Z^2$, $R^4$, $R^5$, $R^6$, $R^7$, $R^8$, Q, t and $R^{16}$ are as defined in formula (I), with a compound of general formula (IX), $NHR^{14}R^{15}$, wherein $R^{14}$ and $R^{15}$ are as defined in formula (I);

and optionally after (a), (b), (c) or (d) forming a pharmaceutically acceptable salt or solvate of the compound of formula (I) obtained.

The processes of the invention may conveniently be carried out in a solvent, e.g. an organic solvent such as an alcohol (e.g. methanol or ethanol), a hydrocarbon (e.g. toluene) or tetrahydrofuran or acetonitrile at a temperature of, for example, 0° C. or above such as a temperature in the range from 0, 5, 10, 15 or 20° C. to 100, 110 or 120° C.

Compounds of formulae (II), (III), (IV), (V), (VI), (VII), (VIII) and (IX) are either commercially available, are well known in the literature or may be prepared easily using known techniques.

It will be appreciated by those skilled in the art that in the process of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) have activity as pharmaceuticals, in particular as modulators of chemokine receptor (especially MIP-1α chemokine receptor) activity, and may be used in the treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions are:

(1) (the respiratory tract) airways diseases including chronic obstructive pulmonary disease (COPD) such as irreversible COPD; asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashiimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease;

(7) cancers, especially non-small cell lung cancer (NSCLC) and squamous sarcoma;

(8) diseases in which angiogenesis is associated with raised chemokine levels; and (9) cystic fibrosis, stroke, re-perfusion injury in the heart, brain, peripheral limbs and sepsis.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating an inflammatory disease which comprises administering to a patient in need thereof a therapeutically effective amount of a compound of formula (I), or a pharmaceutically acceptable salt or solvate thereof, as hereinbefore defined.

The invention still further provides a method of treating an airways disease which comprises administering to a patient in need thereof a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated. The daily dosage of the compound of formula (I) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical is composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

The invention will now be further explained by reference to the following illustrative examples, in which $^1$H NMR spectra were recorded on Varian Unity Inova 400. The central solvent peak of chloroform-d ($\delta_H$ 7.27 ppm) were used as internal standard. Low resolution mass spectra and accurate mass determination were recorded on a Hewlett-Packard 1100 LC-MS system equipped with APCI/ESI ionisation chambers.

All solvents and commercial reagents were laboratory grade and used as received. The nomenclature used for the compounds was generated with ACD/IUPAC Name Pro.

EXAMPLE 1

N-(2-{2-Hydroxy-3-[4-(2-oxo-1,3-benzoxazol-3 (2H)-yl)-1-piperidinyl]propoxy}phenyl)acetamide hydrochloride (i) 3-(4-Piperidinyl)-1,3-benzoxazol-2(3R)-one 2-Aminophenol (0.109 g, 1.0 mmol), tert-butyl 4-oxo-1-piperidinecarboxylate (0.199 mg, 1.0 mmol) and sodium triacetoxyborohydride (0.318 g, 1.5 mmol) in THF-HOAc (20:1, 3.15 ml) was stirred at room temperature for 18 h. The reaction mixture was diluted with dichloromethane, washed with aqueous potassium carbonate (10%), dried ($Na_2SO_4$) and concentrated. The residue was coevaporated with toluene-THF, disolved in THF (10 ml) and carbonyldiimidazole (0.178 g, 1.1 mmol) was added. After stirring for 0.5 h at room temperature the reaction mixture was diluted with dichloromethane, washed with HCl (0.5M) and aqueous sodium bicarbonate, dried ($Na_2SO_4$), and concentrated. The residue in dichloromethane (10 ml) was reacted with trifluoroacetic acid-water (95:5, 3 ml) at room temperature for 15 min. The solution was washed with NaOH (1M), dried ($Na_2SO_4$) and concentrated to give the subtitle compound, which was used in the subsequent step without further purification.

$^1$H-NMR (400 MHz, $CDCl_3$): $\delta$ 7.22-7.07 (m, 4H,), 4.24 (m, 1H), 3.24 (m, 2H), 2.74 (m, 2H), 2.24 (m, 2H), 1.88 (bs, 1H), 1.86 (m, 2H). APCI-MS: m/z 219 [MH$^+$]

(ii) N-(2-{2-Hydroxy-3-[4-(2-oxo-1,3-benzoxazol-3 (2H)-yl)-1-piperidinyl]propoxy}phenyl)acetamide hydrochloride A solution of 3-(4-piperidinyl)-1,3-benzoxazol-2(3H)-one (0.022 g, 0.10 mmol), N-[2-(2-oxiranylmethoxy)phenyl]acetamide (0.021 g, 0.10 mmol) in EtOH (95%, 2 ml) was stirred for 2 hours at 77° C. and over night at room temperature in a sealed vial. The solvent was evaporated and the residue was purified on silica (dichloromethane-methanol, 12:1, containing 1% of NH$_4$OH (25%)). A solution of the purified product in dichloromethane (2 ml) was acidified with HCl (2 M in ether), concentrated, and the residue was coevaporated three times with methanol-toluene to give the title compound (37 mg) as a white powder.

$^1$H-NMR (400 MHz, CD$_3$OD): δ 7.81 (d, 1H), 7.40 (d, 1H), 7.30-7.24 (m, 2H), 7.21-7.13 (m, 2H), 7.07 (d, 1H), 6.98 (bt, 1H), 4.59-4.49 (m, 2H), 4.11 (d, 2H), 3.88 (bd, 2H), 3.44-3.30 (m, 4H), 2.92-2.76 (m, 2H), 2.25-2.14 (m, 2H), 2.21 (s, 3H). APCI-MS: m/z 426 [MH$^+$]

EXAMPLE 2

N-(2-{2-Hydroxy-2-methyl-3-[4-(2-oxo-2,3-dihydro-1H-benzimidazol-1-yl)-1-piperidinyl]propoxy}phenyl)-2-pyridinecarboxamide (i) 2-[(2-Methyl-2-propenyl)oxy]aniline A mixture of 3-chloro-2-methyl-1-propene (5.43 g, 60 mmol), 2-nitrophenol (5.56 g, 40 mmol), potassium carbonate (11.05 g, 80 mmol), tetrabutylammonium hydrogen sulfate (0.271 g, 0.89 mmol) and acetonitrile (120 ml) was heated under reflux for 16 h. The mixture was portioned between toluene and aqueous potassium carbonate (5%), and the organic phase was dried and concentrated. The residue and sodium dithionite (13.9 g, 80 mmol) in EtOH-THF-H$_2$O (2:1:1, 100 ml) was heated under reflux for 3 h and left over the weekend in the fridge. Then, additional sodium dithionite (7 g, 40 mmol) was added and the mixture was boiled for 2 h. The reaction mixture was portioned between dichloromethane and aqueous potassium carbonate (10%) and the organic layer was dried (Na$_2$SO$_4$). Concentrated of the solution gave the subtitle compound.

$^1$H-NMR (300 MHz, CD$_3$OD): δ 6.82-6.65 (m, 4H), 5.05 (d, 2H), 4.47 (s, 2H), 3.83 (bs, 2H), 1.86 (s, 3H). APCI-MS: m/z 164 [MH$^+$]

(ii) 2,2,2-Trifluoro-N-{2-[(2-methyl-2-oxiranyl)methoxy]phenyl}acetamide

A solution of trifluoroacetic acid anhydride (1.7 ml, 12,3 mmol) in dichloromethane (1 ml) was added dropwise to a solution of 2-[(2-methyl-2-propenyl)oxy]aniline (1.0 g, 6.13 mmol) in dichloromethane-pyridine (4:1, 10 ml) at 0° C., and slowly attained room temperature. After 16 h the reaction mixture was cooled to 0° C. and water (1 ml) was added. After 1 h at room temperature the reaction mixture was washed with aqueous potassium carbonate (10%), dried (K$_2$SO$_4$) and concentrated. The residue and 3-chloroperbenzoic acid (75%, 2 g, 9 mmol) in dichloromethane (35 ml) was boiled under reflux for 3 h. The reaction mixture was washed with aqueous potassium carbonate (10%), dried (K$_2$SO$_4$) and concentrated to give the subtitle compound.

$^1$H-NMR (300 MHz, CD$_3$OD): δ 9.72 (bs, 1H), 8.29 (dd, 1H); 7.16 (dt, 1H), 7.07 (dt, 1H), 6.92 (dd, 1H), 4.17 (d, 1H), 4.08 (d, 1H) 2.92 (d, 1H), 2.80 (d, 1H), 1.50 (s, 3H).

(iii) 1-{1-[3-(2-Aminophenoxy)-2-hydroxy-2-methylpropyl]-4-piperidinyl}-1,3-dihydro-2H-benzimidazol-2-one A solution of 1-(4-piperidinyl)-1,3-dihydro-2H-benzimidazol-2-one (1.10 g, 5.05 mmol), 2,2,2-trifluoro-N-{2-[(2-methyl-2-oxiranyl)methoxy]phenyl}acetamide (1.39 g, 5.05 mmol) in EtOH (95%, 20 ml,) was stirred for 2 h at 78° C. Ammonium hydroxide (25%, 7.5 ml) was added to the reaction mixture and heating was continued for additional 5 h. After standing over night at room temperature the reaction mixture was concentrated and the residue was purified on silica (dichloromethane-methanol, 12:1, containing 1% of NH$_4$OH (25%)) to give the subtitle compound (1.54 g).

$^1$H-NMR (400 MHz, CD$_3$OD): δ 9.88 (s, 1H), 7.21 (dd, 1H), 7.12-7.04 (m, 3H), 6.85-6.79 (m, 2H), 6.76-6.70 (m, 2H), 4.31 (m, 1H), 3.91-3.83 (m, 3H), 3.10 (d, 1H), 3.01 (d, 1H), 2.81 (d, 1H), 2.62-2.46 (m, 5H), 1.77 (bt, 2H), 1.55 (bs, 2H), 1.35 (s, 3H). APCI-MS: m/z 397 [MH$^+$]

(iv) N-(2-{2-Hydroxy-2-methyl-3-[4-(2-oxo-2,3-dihydro-1H-benzimidazol-1-yl)-1-piperidinyl]propoxy}phenyl)-2-pyridinecarboxamide HATU in acetonitrile (0.2 M, 0.375 ml, 0.075 mmol) was added to a solution of 1-{1-[3-(2-aminophenoxy)-2-hydroxy-2-methylpropyl]-4-piperidinyl}-1,3-dihydro-2H-benzimidazol-2-one (0.020 g, 0.05 mmol), 2-pyridinecarboxylic acid (0.006 g, 0.05 mmol) and Hünigs base (0.013 ml, 0.075 mmol) in THF (0.5 ml). After 0.5 h at 40° C. and 2 h at room temperature the reaction mixture was concentrated, and the residue purified on silica (dichloromethane-methanol, 12:1, containing 1% of NH$_4$OH (25%)). Yield 20 mg of the title compound.

$^1$H-NMR (400 MHz, CD$_3$OD): δ 8.69 (bd, 1H), 8.39 (bd, 1H), 8.21 (d, 1H), 8.01 (dt, 1H), 7.62-7.58 (m, 1H), 7.24 (m, 1H), 7.16-7.12 (m, 2H), 7.04-6.98 (m, 4H), 4.25 (m, 1H), 4.17 (d, 1H), 4.01 (d, 1H), 3.32 (bs, 1H), 3.17 (bd, 1H), 2.96 (bd, 1H), 2.85 (bs, 1H), 2.63-2.48 (m, 4H), 1.67 (bt, 2H), 1.48 (s, 3H). APCI-MS: m/z 502 [MH$^+$]

EXAMPLE 3

N-(2-{2-Hydroxy-3-[4-(2-oxo-2,3-dihydro-1H-benzimidazol-1-yl)-1-piperidinyl]propoxy}phenyl)benzamide hydrochloride (i) 1-{1-[3-(2-Aminophenoxy)-2-hydroxypropyl]-4-piperidinyl}-1,3-dihydro-2H-benzimidazol-2-one A solution of 1-(4-piperidinyl)-1,3-dihydro-2H-benzimidazol-2-one (0.434 g, 2.0 mmol), 2-[(2-nitrophenoxy)methyl]oxirane (0.390 g g, 2.0 mmol) in EtOH (95%, 3 ml, was stirred for 2 hours at 78° C. The reaction mixture was cooled and Pd—C (5%, 0.20 g) was added. Then ammonium formiate (1.26 g, 20 mmol) was added in portions during 5 min. After 90 min the reaction mixture was filtered through Celite, concentrated, partioned between dichloromethane and ammonium hydoxide (25%) and purified on silica (dichloromethane-methanol, 12:1, containing 1% of NH$_4$OH (25%)) to give the subtitle compound.

$^1$H-NMR (400 MHz, CD$_3$OD): δ 7.41-7.37 (m, 1H), 7.08-7.02 (m, 3H), 6.86 (dd, 1H), 6.77-6.72 (m, 2H), 6.70-6.65 (m, 1H), 4.36-4.27 (m, 1H), 4.21-4.15 (m, 1H), 4.06 (dd, 1H), 3.96 (dd, 1H), 3.20 (bt, 2H), 2.71-2.49 (m, 4H), 2.32 (bq, 2H), 1.755 (bd, 2H).

(ii) N-(2-{2-Hydroxy-3-[4-(2-oxo-2,3-dihydro-1H-benzimidazol-1-yl)-1-piperidinyl]propoxy}phenyl)benzamide hydrochloride-2-one Benzoylchloride (0.006 ml, 0.052 mmol) was added to a solution of 1-{1-[3-(2-aminophenoxy)-2-hydroxypropyl]4-piperidinyl}-1,3-dihydro-2H-benzimidazol-2-one (0.020 g, 0.052 mmol) and Hünigs base (0.018 ml, 0.105 mmol) in THF (1.5 ml) at 0° C. The reaction was left over night at room temperature, concentrated and purified on silica (dichloromethane-methanol, 12:1, containing 1% of NH$_4$OH (25%). A solution of the purified product in methanol (2 ml) was acidified with HCl (1M) to pH 3, concentrated, and the residue was coevaporated three times with ethanol-toluene to give the title compound.

$^1$H-NMR (400 MHz, CD$_3$OD): δ 8.00 (bd, 2H), 7.77 (bd, 1H), 7.64-7.53 (m, 3H), 7.31-7.20 (m, 3H), 7.18-7.06 (m, 4H), 4.54-4.47 (m, 1H), 4.46-4.41 (m, 1H), 4.19-4.14 (m, 2H), 3.77-3.61 (m, 2H), 3.29-3.04 (m, 4H), 2.87-2.74 (m, 2H), 2.04-1.95 (bs, 2H). APCI-MS: m/z 487 [MH$^+$]

The compounds of Examples 4 to 29 were prepared by routes analogous to those described in the previous Examples.

EXAMPLE 4

2-{2-Hydroxy-3-[4-(2-oxo-2,3-dihydro-1H-benzimidazol-1-yl)-1-piperidinyl]propoxy}-N-methylbenzamide APCI-MS: m/z 425 [MH$^+$]

EXAMPLE 5

N-[2-(2-Hydroxy-3-{4-[2-oxo-5-(trifluoromethyl)-2,3-dihydro-1H-benzimidazol-1-yl]-1-piperidinyl}propoxy)phenyl]acetamide APCI-MS: m/z 493 [MH$^+$]

EXAMPLE 6

N-(2-{3-[4-(6-Chloro-2-oxo-2,3-dihydro-1H-benzimidazol-1-yl)-1-piperidinyl]-2-hydroxypropoxy}phenyl)-4-methylbenzamide APCI-MS: m/z 535 [MH$^+$]

EXAMPLE 7

4-Chloro-N-[2-(2-hydroxy-3-{4-[2-oxo-5-trifluoromethyl)-2,3-dihydro-1H-benzimidazol-1-yl]-1-piperidinyl}propoxy)phenyl]benzamide APCI-MS: m/z 589 [MH$^+$]

EXAMPLE 8

N-[2-({(2R)-3-[4-(5-Fluoro-2-oxo-2,3-dihydro-1H-benzimidazol-1-yl)-1-piperidinyl]-2-hydroxypropyl}oxy)phenyl]acetamide hydrochloride APCI-MS: m/z 443 [MH$^+$]

EXAMPLE 9

N-(2-{3-[4-(5-Fluoro-2-xo-2,3-dihydro-1M-benzimidazol-1-yl)-1-piperidinyl]-2-hydroxypropoxy}phenyl)benzamide APCI-MS: m/z 505 [MH$^+$]

EXAMPLE 10

N-[2-({(2S)-3-[4-(5-Fluoro-2-oxo-2,3-dihydro-1H-benzimidazol-1-yl)-1-piperidinyl]-2-hydroxypropyl}oxy)phenyl]acetamide hydrochloride APCI-MS: m/z 443 [MH$^+$]

EXAMPLE 11

N-(2-{3-[4-(5-Fluoro-2-oxo-2,3-dihydro-1H-benzimidazol-1-yl)-1-piperidinyl]-2-hydroxypropoxy}phenyl)acetamide APCI-MS: m/z 443 [MH$^+$]

EXAMPLE 12

N-(2-{3-[4-(6-Chloro-2-oxo-2,3-dihydro-1H-benzimidazol-1-yl)-1-piperidinyl]-2-hydroxypropoxy}phenyl)acetamide APCI-MS: n/z 459 [MH$^+$]

EXAMPLE 13

N-(2-{3-[4-(5-Fluoro-2-oxo-2,3-dihydro-1-benzimidazol-1-yl)-1-piperidinyl]-2-hydroxypropoxy}phenyl)-4-methoxybenzamide APCI-MS: m/z 535 [MH$^+$]

EXAMPLE 14

N-[2-(2-Hydroxy-3-{4-[2-oxo-5-(trifluoromethyl)-2,3-dihydro-1H-benzimidazol-1-yl]-1-piperidinyl}propoxy)phenyl]benzamide APCI-MS: m/z 555 [MH$^+$]

EXAMPLE 15

4-Chloro-N-2-{3-[4-(6-chloro-2-oxo-2,3-dihydro-1H-benzimidazol-1-yl)-1-piperidinyl]-2-hydroxypropoxy}phenyl)benzamide APCI-MS: m/z 555 [MH$^+$]

EXAMPLE 16

N-(2-{2-Hydroxy-3-[4-(2-oxo-1,3-benzoxazol-3(2H)-yl)-1-piperidinyl]propoxy}phenyl)-4-methylbenzamide APCI-MS: m/z 502 [MH$^+$]

EXAMPLE 17

N-(2-{2-Hydroxy-2-methyl-3-[4-(2-oxo-2,3-dihydro-1H-benzimidazol-1-yl)-1-piperidinyl]propoxy}phenyl)acetamide APCI-MS: m/z 439 [MH$^+$]

EXAMPLE 18

4-Chloro-N-(2-{3-[4-(5-fluoro-2-oxo-2,3-dihydro-1H-benzimidazol-1-yl-1-piperidinyl]-2-hydroxypropoxy}phenyl)benzamide APCI-MS: m/z 539 [MH$^+$]

EXAMPLE 19

N-(2-{2-Hydroxy-3-[4-(2-oxo-1,3-benzoxazol-3(2H)-yl)-1-piperidinyl]propoxy}phenyl)benzamide APCI-MS: m/z 488 [MH$^+$]

EXAMPLE 20

N-(2-{3-[4-(5-Fluoro-2-oxo-2,3-dihydro-1H-benzimidazol-1-yl)-1-piperidinyl]-2-hydroxypropoxy}phenyl)-4-methylbenzamide APCI-MS: m/z 519 [MH$^+$]

EXAMPLE 21

N-(2-{2-Hydroxy-3-[4-(2-oxo-2,3-dihydro-1H-benzimidazol-1-yl)-1-piperidinyl]propoxy}phenyl)acetamide hydrochloride APCI-MS: m/z 425 [MH$^+$]

EXAMPLE 22

4-Chloro-N-(2-{2-hydroxy-3-[4-(2-oxo-1,3-benzoxazol-3(2H)-yl)-1-piperidinyl]propoxy}phenyl)benzamide APCI-MS: m/z 522 [MH$^+$]

EXAMPLE 23

4-Chloro-N-2-{2-hydroxy-3-[4-(2-oxo-2,3-dihydro-1-benzimidazol-1-yl)-1-piperidinyl]propoxy}phenyl)benzamide APCI-MS: m/z 522 [MH$^+$]

EXAMPLE 24

N-(2-{2-Hydroxy-2-methyl-3-[4-(2-oxo-2,3-dihydro-1H-benzimidazol-1-yl)-1-piperidinyl]propoxy}phenyl)benzamide APCI-MS: m/z 501 [MH$^+$]

EXAMPLE 25

N-(2-{3-[4-(5-Fluoro-2-oxo-2,3-dihydro-1H-benzimidazol-1-yl)-1-piperidinyl]-2-hydroxypropoxy}phenyl)-5-isoxazolecarboxamide APCI-MS: m/z 496 [MH$^+$]

EXAMPLE 26

N-(2-{2-Hydroxy-3-[4-(2-oxo-1,3-benzoxazol-3(2H)-yl)-1-piperidinyl]propoxy}phenyl)acetamide APCI-MS: m/z 4261 [MH$^+$]

EXAMPLE 27

N-(2-{2-Hydroxy-3-[4-(2-oxo-2,3-dihydro-1H-benzimidazol-1-yl)-1-piperidinyl]propoxy}phenyl)acetamide APCI-MS: m/z 425 [MH$^+$]

EXAMPLE 28

N-(2-{2-Hydroxy-3-[4-(2-oxo-2,3-dihydro-1H-benzimidazol-1-yl)-1-piperidinyl]propoxy}phenyl)-4-methylbenzamide APCI-MS: m/z 501 [MH$^+$]

EXAMPLE 29

2-{3-[4-(5-Fluoro-2-ox-2,3-dihydro-1H-benzimidazol-1-yl)-1-piperidinyl]-2-hydroxypropoxy}-N-methylbenzamide APCI-MS: m/z 443 [MH$^+$]

EXAMPLE 30

N-[4-Fluoro-2-({(2S)-3-[4-(5-fluoro-2-oxo-2,3-dihydro-1H-benzimidazol-1-yl)-1-piperidinyl]-2-hydroxypropyl}oxy)phenyl]acetamide trifluoroacetate i) (2S)-2-[(5-Fluoro-2-nitrophenoxy)methyl]oxirane In a flask was added (R)-glycidol (0.994 g, 13.4 mmole) and triphenylphosphine (3.52 g, 13.4 mmole) and THF (20 ml, dried over molecular sieves), and 5-fluoro-2-nitrophenol (2.10 g, 13.4 mmole). The mixture was stirred until a homogeneous solution was obtained. The solution was cooled in an ice bath and diethylazodicarboxylate (DEAD, 2.11 ml, 13.4 mmole) was added dropwise over a few minutes. After completed addition, the flask was allowed to reach room temperature and stirred for an additional 2 hours. The solvent was removed in vaccuo and to the residue was added chloroform (5-10 ml). The precipitate (PPh$_3$O) was removed by filtration and the solid was washed with an additional amount of chloroform (5-10 ml). The filtrate was added to a flash column (SiO$_2$, Heptane:Ethyl acetate 4:1), and purified to give 2.02 g (71%) of the sub-title compound as a crystalline material after concentration of pure fractions.

$^1$H-NMR (400 MHz, CDCl$_3$) δ: 7.97 (1H, dd, J 9.3, 6.0 Hz); 6.86 (1H, dd, J 10.0, 2.5 Hz); 6.80-6.74 (1H, m); 4.44 (1H, dd, J 11.4, 2.6 Hz); 4.12 (1H, dd, J 11.2, 5.1 Hz); 3.44-3.38 (1H, m); 2.95 (1H, t, J=4.5 Hz); 2.90 (1H, dd, J 4.8, 2.6)

ii) N-{4-Fluoro-2-[(2S)oxiranylmethoxy]phenyl}acetamide (2S)-2-[(5-fluoro-2-nitrophenoxy)methyl]oxirane (0.32 g, 1.5 mmol) was dissolved in ethyl acetate (40 ml). Platinum on charcoal (0.15 g) was added, and the mixture was stirred in the atmosphere of hydrogen for 3 h at room temperature and atmospheric pressure. The catalyst was filtered and washed on the filter with ethyl acetate (10 ml). Acetic anhydride (0.31 g, 0.28 ml, 3 mmol) and ethyldi(i-propyl)amine (0.39 g, 0.52 ml, 3 mmol) were added to the solution. The reaction mixture was stirred at room temperature for 3 h, then washed with 1M sodium hydroxide (NaOH) (30 ml) and brine (30 ml), and dried with sodium sulphate ($Na_2SO_4$). Evaporation of the solvent and flash chromatography on silica gel with n-heptane/ethyl acetate (from 25 to 75%) afforded the subtitle compound (0.21 g, 0.92 mmol, 61%) as a colourless solid.

APCI-MS: m/z 226 [MH$^+$]. $^1$H-NMR (400 MHz, $CDCl_3$): δ 8.30 (dd, 1H, J=9.0, J=5.2), 7.71 (br.s, 1H), 6.6-6.8 (m, 2H), 4.37 (dd, 1H, J=11.3, J=2.3), 3.90 (dd, 1H, J=11.3, J=6.3), 3.40 (m, 1H), 2.97 (t, 1H, J=4.4), 2.78 (dd, 1H, J=4.8, J=2.7), 2.21 (s, 3H).

iii) N-[4-Fluoro-2-({(2S)-3-[4-(5-fluoro-2-oxo-2,3-dihydro-1H-benzimidazol-1-yl]-1-piperidinyl]-2-hydroxypropyl}oxy)phenyl]acetamide trifluoroacetate A solution of 5-fluoro-1-(4-piperidinyl)-1,3-dihydro-2H-benzimidazol-2-one (100 mg, 0.42 mmol, prepared by analogy to Example 1 i)) and N-{4-fluoro-2-[(2S)oxiranylmethoxy]phenyl}acetamide (96 mg, 0.42 mmol) in ethanol (5 ml, 99.5%) was refluxed for 3 h. The solvent was distilled off under reduced pressure. The residue was purified by preparative HPLC (Kromasil column; eluent: [acetonitrile+ 0.1% trifluoroacetic acid (TFA)/water+0.1% TFA]) to afford a colourless solid (229 mg, 0.40 mmol, 95%).

APCI-MS: m/z 461 [MH$^+$]. $^1$H-NMR (400 MHz, DMSO-$d_6$): δ 11.16 (s, 1H), 9.83 (br. s, 1H), 9.10 (s, 1H), 7.83 (t, 1H, J=8.4), 7.37 (m, 1H), 6.7-7.0 (m, 4H), 4.56 (m, 1H), 4.40 (m, 1H), 4.00 (m, 2H), 3.73 (d, 2H, J=11.2), 3.0-3.4 (m, 4H), 2.6-2.8 (m, 2H), 2.09 (s, 3H), 1.92 (t, 2H, J=14.0).

EXAMPLE 31

5-Fluoro-1-(1-{(2S)-2-hydroxy-3-[(2-methyl-1,3-benzoxazol-4-yl)oxy]propyl}-4-piperidinyl)-1,3-dihydro-2H-benzimidazol-2-one trifluoroacetate i) 2-Methyl-4-[(2S)oxiranylmethoxy]-1,3-benzoxazole

A suspension of 2-methyl-1.3-benzaxozol-4-ol (0.146 g, 0.98 mmol) (P. Crabbe, A. Villarino and J. M. Muchowski, *J.Chem.Soc.Perk.I*, 1973,2220-2222.), (2S)-2-[(3-nitrophenoxy)methyl]oxirane (0-192 g, 1.08 mmol) and cesium carbonate (0.478 g, 1.47 mmol) in dry dimethylformamide (DMF) (4 mL) was stirred at room temperature for 4 hours. More of the oxirane (0.04 g, 0.2 mmol) was added and the reaction continued for an additional hour. The reaction mixture was partitioned between ethyl acetate and saturated aqueous sodium chloride. The aqueous phase was extracted with ethyl acetate and the combined organic phase was washed three times with water, dried and concentrated. The residue was purified by flash chromatography (silica gel, dichloromethane-ethyl acetate, 10:1) to afford the subtitle compound (0.14 g, 69.6%) as a colourless oil which solidified upon drying.

APCI-MS: m/z 206 [MH$^+$]$^1$H-NMR (300 MHz, $CDCl_3$): δ 7.18 (t, 1 H, J=8.0 Hz), 7.09 (dd, 1H, J=1.0 and 8.2 Hz), 6.79 (dd, 1H, J=0.8 and 8.0 Hz), 4.45 (dd, 1H, J=3.7 and 11.2 Hz), 4.29 (dd, 1H, J=5.6 and 11.2 Hz), 3.44 (m, 1H), 2.91 (t, 1H, J=36.6 Hz), 2.76 (dd, 1H, J=2.6 and 5.0 Hz) and 2.60 (s, 3H).

ii) 5-Fluoro-1-(1-{(2S)-2-hydroxy-3-[(2-methyl-1,3-benzoxazol-4-yl)oxy]propyl}-4-piperidinyl)1,3-dihydro-2H-benzimidazol-2-one trifluoroacetate The title compound was prepared according to the procedure described in Example 30 from 5-fluoro-1-(4-piperidinyl)-1,3-dihydro-2H-benzimidazol-2-one and 2-methyl-4-[(2S)oxiranylmethoxy]-1,3-benzoxazole. Yield 72%.

APCI-MS: m/z 441 [MH$^+$]. $^1$H-NMR (400 MHz, DMSO-$d_6$):δ 11.14 (s, 1H), 9.58 (br. s, 1H), 9.10 (s, 1H), 7.2-7.4 (m, 3H), 6.7-7.0 (m, 3H), 4.54 (m, 1H), 4.39 (m, 1H), 4.26 (m, 2H), 3.71 (m, 2H), 3.0-3.4 (m, 4H), 2.5-2.8 (m, 2H), 2.57 (s, 3H), 1.91 (t, 2H, J=14.0).

EXAMPLE 32

N-[2-{(2S)-3-[4-(5-Fluoro-2-oxo-2,3-dihydro-1-benzimidazol-1-yl]-1-piperidinyl]-2-hydroxypropyl}oxy)-4-methoxyphenyl]acetamide i) N-(2-Hydroxy-4-methoxyphenyl)acetamide

2-Nitro-5-methoxyphenol (R. J. Maleski, *Synthetic Communications*, 23(3), 343-348 (1993)) (48.5 g, 0.287 mol) dissolved in tetrahydrofuran (THF) (1.5 L) was hydrogenated at ambient temperature over night with 10% Pd/C (10 g) until 20.3 L of hydrogen was consumed. After filtration and evaporation the residue was suspended in degased water (1.7 L) and acetic anhydride (42.5 mL) was added with stirring. The mixture was heated to 60° C. for 1 h and then cooled. The isolated solid was washed thoroughly with water and dried in vacuo to give brick-red crystals (41.7 g, 80%).

$^1$H-NMR (400 MHz, $CDCl_3$): δ 8.98 (s, 1H); 7.34 (bs, 1H); 6.81 (d, 1H); 6.58 (d, 1H); 6.44 (dd, 1H); 3.78 (s, 3H); 2.26 (s, 3H)

ii) N-{4-Methoxy-2-[(2S)oxiranylmethoxy]phenyl}acetamide

N-2-Hydroxy 4-methoxyphenyl)acetamide (18.12 g, 0.1 mol) and S-(+)-glycidyl nosylate (25.92 g, 0.1 mol) were dissolved in dry dimethylformamide (DMF) (75 mL) and stirred under $N_2$ on an ice-bath. Cesiumcarbonate (35.8 g, 0.11 mmol) was added and stirring under $N_2$ was continued at ambient temperature overnight. The mixture was poured into ethylacetate (1 L) and water (250 mL). The organic phase was washed with water (3×250 mL), dried and evaporated to give an orange solid crude product (29 g), which was recrystallized from ethanol (100 mL) and washed with ether to give white crystals. More white crystals were obtained from the mother liquor, after evaporation and recrystallization from 2-propanol. Total yield 15 g (63°/).

$^1$H-NMR ($CDCl_3$): δ 8.22 (d, 1H); 7.64 (bs, 1H); 6.53 (dd, 1H); 6.50 (d, 1H); 4.34 (dd, 1H); 3.92 (dd, 1H); 3.79 (s, 3H); 3.38 (m, 1H); 2.96 (t, 1H); 2.78 (dd, 1H); 2.20 (s, 3H)

iii) N-[2-({(2S)-3-[4-(5-Fluoro-2-oxo-2,3-dihydro-1H-benzimidazol-1-yl]-1-piperidinyl]-2-hydroxypropyl}oxy)-4-methoxyphenyl]acetamide The title compound was prepared according to the procedure described in Example 30 above from 5-fluoro-1-(4-piperidinyl)-1,3-dihydro-2H-benzimidazol-2-one and N-{4-methoxy-2-[(2S)oxiranylmethoxy]phenyl}acetamide. The product was purified by preparative HPLC (Kromasil column; eluent: acetonitrile/water) to afford a colourless solid (84%).

APCI-MS: m/z 473 [MH$^+$]. $^1$H-NMR (400 MHz, DMSO-d$_6$): δ 10.99 (s, 1H), 8.92 (s, 1H), 7.76 (d, 1H, J=8.9), 7.19 (dd, 1H, J=8.6, J=4.5), 6.7-6.9 (m, 2H), 6.64 (d, 1H, J=2.5), 6.48 (dd, 1H, J=8.9, J=2.5), 5.05 (br. s, 1H), 4.0-4.2 (m, 3H), 3.9 (m, 1H), 3.73 (s, 3H), 3.08 (d, 1H, J=10.9), 3.01 (d, 1H, J=10.9), 2.54 (s, 2H), 2.1-2.5 (m, 5H), 2.06 (s, 3H), 1.62 (d, 2H, J=11.0)

EXAMPLE 33

2-{3-[4-(5-Fluoro-2-oxo-2,3-dihydro-benzoimidazol-1-yl)piperidin-1-yl]-2-hydroxy-propoxy}-N-cyclopropyl-benzamide i) (S)-2-{3-[4-(5-Fluoro-2-oxo-2,3-dihydro-benzoimidazol-1-yl)piperidin-1-yl]-2-hydroxy-propoxy}-benzoic acid tert-butyl ester A solution of 5-fluoro-1-piperidin-4-yl-1,3-dihydro-benzoimidazol-2-one (235 mg, 0.5 mmol) and 2-oxiranylmethoxy-benzoic acid tert-butyl ester (250 mg, 1.0 mmol) in isopropanol (iPrOH) (10 mL) was stirred at 70° C. for 14 h, after which the solvent was removed in vacuo. The residue was purified by gradient flash chromatography on silica gel (CH$_2$Cl$_2$ to EtOH), yielding an off-white solid (240 mg, 99%).

APCI-MS: m/z 486 [MH$^+$].

ii) 2-{3-[4-(5-Fluoro-2-oxo-2,3-dihydro-benzoimidazol-1-yl)piperidin-1-yl]-2-hydroxy-propoxy}-N-cyclopropyl-benzamide A solution of (S)-2-{3-[4-(5-fluoro-2-oxo-2,3-dihydro-benzoimidazol-1-yl)pipereidin-1-yl]-2-hydroxy-propoxy}-benzoic acid tert-butyl ester (240 mg, 0.5 mmol) and conc. HCl (0.5 mL) in CHCl$_3$ (2 mL) and CH$_2$Cl$_2$ (15 mL) was stirred at room temperature for 17 h, after which the solvent was removed in vacuo. The residue was redissolved in H$_2$O/acetonitrile. Freeze-drying afforded the carboxylic acid intermediate as a red solid (210 mg; 99%). APCI-MS: m/z 430 [MH$^+$].

To a suspension of polymer supported carbodiimide in 20% DMF/CH$_2$Cl$_2$ (5 mL), cyclopropylamine (7.0 mg, 0.12 mmol) and the above afforded carboxylic acid intermediate (50 mg, 0.12 mmol) were added subsequently. The reaction mixture was shaken for 17 h, after which it was filtrated. The beads were washed with CH$_2$Cl$_2$ and the combined organic layers removed in vacuo. The residue was purified using HPLC (Kromasil column; acetonitrile+0.1% TFA/H$_2$O+0.1% TFA) to afford white solid (4 mg, 6%).

APCI-MS: m/z 469 [MH$^+$].

EXAMPLE 34

2-{3-[4-(5-Fluoro-2-oxo-2,3-dihydro-benzoimidazol-1-yl)piperidin-1-yl]-2-hydroxy-propoxy}-N-3-hydroxy-pyridin-2-yl)-benzamide The title was prepared by a process analogous to that used in Example 33. Purification using HPLC yielded a white solid (12 mg, 15%).

APCI-MS: m/z 522 [MH$^+$].

EXAMPLE 35

N-[2-({(2S)-3-[4-(5-Chloro-2-oxo-2,3-dihydro-1H-benzimidaol-1-yl)-1-piperidinyl]-2-hydroxypropyl}oxy)phenyl]acetamide(trifluoroacetate)

i) 4-(4-Chloro-2-nitro-phenylamino)-piperidine-1-carboxylic acid tert-butyl ester A suspension of 4-amino-piperidine-1-carboxylic acid tert-butyl ester. HCl (2.00 g, 10.0 mmol), 4-chloro-1-fluoro-2-nitrobenzene (1.75 g, 10.0 mmol) and cesium carbonate (6.50 g, 20.0 mmol) in THF (20 ml) was stirred at 75° C. for 36 h. After filtration the solvent was removed in vacuo, yielding a bright orange oil (3.23 g, 9.1 mmol, 90%).

APCI-MS: m/z 256 [MH$^+$-BOC]. $^1$H-NMR (300 MHz, CDCl$_3$): δ 8.17 (d, 1H, J=2.6), 8.06-8.03 (m, 1H), 7.38-7.34 (m, 1H), 6.83 (d, 1H, J=9.4), 4.04-4.00 (m, 2H), 3.65-3.63 (m, 1H), 3.08-3.00 (m, 2H), 2.07-2.01 (m, 2H), 1.64-1.49 (m, 2H), 1.46 (s, 9H).

ii) 4-(5-Chloro-2-oxo-2,3-dihydro-benzoimidazol-1-yl-piperidine-1-carboxylic acid tert-butyl ester A suspension of 4-(4-chloro-2-nitro-phenylamino)-piperidine-1-carboxylic acid tert-butyl is ester (3.23 g, 9.0 mmol) and platinum on charcoal 5% (1.0 g) in THF (120 ml) was hydrogenated for 1 h at 50 psi at room temperature. After filtration the solvent was removed in vacuo, yielding a deep purple oil (2.72 g, 8.4 mmol, 84%), APCI-MS: m/z 226 [MH$^+$BOC$^-$], which was redissolved in THF (50 mL). 1,1-carbonyldiimidazole (1.63 g, 10.0 mmol) was added and the reaction mixture was stirred for 48 h at room temperature. The solvent was removed in vacuo and the residue purified by gradient flash chromatography on silica gel (CH$_2$Cl$_2$ to EtOH), yielding an off-white solid (1.85 g, 63%).

APCI-MS: m/z 252 [MH$^+$BOC$^-$]; $^1$H-NMR (300 MHz, CDCl$_3$): δ 10.19 (s, 1H), 7.13 (s, 1H), 7.03 (s, 2H), 4.49-4.31 (m, 3H), 2.91-2.83 (m, 2H), 2.33-2.22 (m, 2H), 2.84 (m, 2H), 1.50 (s, 9H).

iii) 5-Chloro-1-piperidin-4-yl-1,3-dihydro-benzoimidazol-2-one

A solution of 4-(5-chloro-2-oxo-2,3-dihydro-benzoimidazol-1-yl)-piperidine-1-carboxylic acid tert-butyl ester (1.50 g, 4.3 mmol) and H$_2$O/TFA 5% (15 mL) in CH$_2$Cl$_2$ (20 ml) was stirred at room temperature for 1 h, after which the solvent was removed in vacuo. The residue was purified by gradient flash chromatography on silica gel (CH$_2$Cl$_2$ to EtOH), yielding an off-white/pinkish solid (0.97 g, 90%).

APCI-MS: m/z 252 [MH$^+$]; $^1$H-NMR (300 MHz, CDCl$_3$): δ 11.12 (s, 1H), 7.30-7.28 (m, 1H), 7.08-7.02 (m, 2H), 4.53-4.45 (m, 1H), 3.10-3.04 (m, 2H), 2.55-2.44 (m, 2H), 1.89-1.74 (m, 2H).

iv) N-[2-({(2S)-3-[4-(5-Chloro-2-oxo-2,3-dihydro-1H-benzimidazol-1-yl)-1-piperidinyl]-2-hydroxypropyl}oxy)phenyl]acetamide(trifluoroacetate)

A mixture of N-{2-[(2S)oxiranylmethoxy]phenyl}acetamide (85 mg, 0.41 mmol), 5-chloro-1-(4-piperidinyl)-1,3-dihydro-2H-benzimidazol-2-one, trifluoroacetate (150 mg, 0.41 mmol), K$_2$CO$_3$ (62 mg, 0.45 mmol) in ethanol (3 mL) was kept under stirring at 80° C. for 2.5 h.

The reaction mixture was cooled to room temperature and partitioned between ethylacetate and water, organic phase dried over $Na_2SO_4$, filtered and concentrated. The residue was purified by reverse phase HPLC to give the title compound (47 mg).

APCI-MS: m/z 459 (MH+). $^1$H-NMR (DMSO-$d_6$, 400 MHz): δ 11.22 (s, 1H); 9.50 (br.s, 1H); 9.00 (s, 1H); 7.90 (d, J=8.2 Hz, 1H); 7.41 (d, J=8.5 Hz, 1H); 7.05 (m, 4H); 6.93 (m, 1H); 6.08 (br.s, 1H); 4.56 (m, 1H); 4.38 (m, 1H); 4.00 (m, 2H); 3.65 (m, 2H); 3.28 (m, 2H); 3.19 (m, 2H); 2.75 (m, 1H); 2.63 (m, 1H); 2.10 (s, 3H); 1.90 (m, 2H).

EXAMPLE 36

2-({(2S)-3-[4-(5-Chloro-2-oxo-2,3-dihydro-1H-benzimidazol-1-yl]-1-piperidinyl]-2-hydroxypropyl}-N-cyclopropylbenzamide(trifluoroacetate)

A mixture of N-cyclopropyl-2-[(2S)oxiranylmethoxy)benzamide (96 mg, 0.41 mmol), 5-chloro-1-(4-piperidinyl)-1,3-dihydro-2H-benzimidazol-2-one, trifluoroacetate (see Example 35: i-iv) (150 mg, 0.41 mmol), $K_2CO_3$ (62 mg, 0.45 mmol) in ethanol (3 mL) was kept under stirring at 80° C. for 2.5 h. The reaction mixture was cooled to room temperature and partitioned between ethylacetate and water, organic phase dried over $Na_2SO_4$, filtered and concentrated. The residue was purified by reverse phase HPLC to give the title compound (77 mg).

APCI-MS: m/z 485 (MH+). $^1$H-NMR (DMSO-$d_6$, 400 MHz): δ 11.18 (s, 1H); 9.50 (br.s, 1H); 8.28 (d, J=5.4 Hz, 1H); 7.65 (dd, J=1.7, 7.6 Hz, 1H); 7.46 (m, 1H); 7.40 (d, J=8.5 Hz, 1H); 7.10 (m, 4H); 6.18 (br s, 1H); 4.60 (m, 1H); 4.39 (m, 1H); 4.18 (m, 2H); 3.75 (m, 2H); 3.30 (m, 4H); 2.95 (m, 1H); 2.70 (m, 2H); 1.98 (m, 1H); 0.71 (m, 2H); 0.55 (m, 2H).

EXAMPLE 37

N-2-{3-[4-(5-Chloro-2-oxo-2,3-dihydro-benzoimidazol-1-yl)piperidin-1-yl]-2-hydroxy-propoxy}-4-fluoro-phenyl)-acetamide A solution of 5-chloro-1-piperidin-4-yl-1,3-dihydro-benzoimidazol-2-one (125 mg, 0.5 mmol) and N-(4-fluoro-2-oxiranylmethoxy-phenyl)-acetamide (120 mg, 0.5 mmol) in isopropanol (i-PrOH) (5 mL) were stirred at 70° C. for 17 h, after which the solvent was removed in vacuo. The residue was purified using HPLC (Kromasil column; acetonitrile+0.1% TFA/$H_2O$+0.1% TFA) to afford a white solid (71 mg, 24%).

APCI-MS: m/z 477 [MH+].

EXAMPLE 38

N-(5-Chloro-2-{3-[4-(5-fluoro-2-oxo-2,3-dihydro-benzoimidazol-1-yl)piperidin-1-yl]-2-hydroxy-propoxy}-phenyl)-acetamide A solution of 5-fluoro-1-piperidin-4-yl-1,3-dihydro-benzoimidazol-2-one (480 mg, 2.0 mmol) and N-(5-chloro-2-oxiranylmethoxy-phenyl)-acetamide (490 mg, 2.0 mmol) in isopropanol (i-PrOH) (10 mL) and EtOH (10 mL) were stirred at 80° C. for 17 h, after which the solvent was removed in vacuo. The residue was purified using gradient flash chromatography ($CH_2Cl_2$ to MeOH), yielding the desired product as a white solid (960 mg, 99%).

APCI-MS: m/z 477 [MH+].

EXAMPLE 39

5-Fluoro-1-(1-{(2S)-2-hydroxy-3-[(2-methyl-1H-indol-7-yl)oxy]propyl}4-piperidinyl)-1,3-dihydro-2H-benzimidazol-2-one (i) 1-(Benzhydryloxy)-2-nitrobenzene A mixture of o-nitrophenol (2.08 g, 15.0 mmol), 1-[bromo(phenyl)methyl]benzene (3.70 g, 15.0 mmol) and potassium carbonated ($K_2CO_3$) (4.14 g, 30.0 mmol) in acetone (60 mL) was kept at reflux temperature for 5 h. The reaction mixture was cooled to room temperature, concentrated in vacuo. The residue was partitioned between dichloromethane ($CH_2Cl_2$) and water ($H_2O$), organic layer dried over sodium sulphate ($Na_2SO_4$), filtered, concentrated. The residue was purified by silica gel flash chromatography to give subtitled compound (1.81 g).

$^1$H-NMR (DMSO-$d_6$, 400 MHz): δ 7.87 (dd, J=1.6, 8.1 Hz, 1H); 7.51 (br.d, J=7.2 Hz, 5H); 7.35 (m, 5H); 7.26 (m, 2H); 7.05 (m, 1H); 6.84 (s, 1H).

(ii) Benzhydryl-2-methyl-1H-indol-7-yl-ether

To a solution of 1-(benzhydryloxy)-2-nitrobenzene (500 mg, 1.63 mmol) in tetrahydrofuran (5 mL) was added 0.5 M THF solution of isopropenylmagnesium bromide slowly at −45° C. After addition was complete the reaction mixture was kept on stirring at −45° C. for 40 min, then reaction mixture poured into aqueous ammonium chloride ($NH_4Cl$) solution which was extracted with dichloromethane ($CH_2Cl_2$). The organic layer was washed with water ($H_2O$), dried over sodium sulphate ($Na_2SO_4$), filtered, concentrated and the residue purified by silica gel flash chromatography to give the subtitled compound (85 mg).

APCI-MS: m/z 314 (MH+).
$^1$H-NMR (CDCl$_3$, 400 MHz): δ 8.18 (br.s, 1H); 7.50-7.25 (m, 10H); 7.12 (d, J=7.9 Hz, 1H); 6.86 (t, J=7.8 Hz, 1H); 6.52 (d, J=7.8 Hz, 1H); 6.39 (s, 1H); 6.20 s, 1H); 2.43 (s, 3H).

(iii) 2-Methyl-1H-indol-7-ol

Benzhydryl-2-methyl-1H-indol-7-yl-ether (85 mg, 0.271 mmol) in methanol (MeOH) (3 mL) and toluene (3 mL) was hydrogenated in the presence of 20% palladium hydroxide (Pd(OH)$_2$) (40 mg) at 40 p.s.i for 70 min at room temperature. The catalyst was filtered off, filtrate concentrated and the residue purified by silica gel flash chromatography to give subtitled compound (20 mg).

$^1$H-NMR (CDCl$_3$, 400 MHz): δ 8.18 (br.s, 1H); 7.14 (d, J=7.9 Hz, 1H); 6.90 (t, J=7.8 Hz, 1H); 6.52 (d, J=7.4 Hz, 1H); 6.21 (s, 1H); 2.44 (s, 3H). APCI-MS: m/z 148 (MH+).

(iv) 2-Methyl-7-[(2S)-oxiranylmethoxy]-1H-indole

A mixture of (2S)-2{[(3-nitrophenyl)sulfonyl]methyl}oxirane (39 mg, 0.15 mmol), 2-methyl-1H-indol-7-ol (15 mg, 0.1 mmol), caesium carbonate ($Cs_2CO_3$) (65 mg, 0.2 mmol) in DMF (1.5 mL) was kept on stirring at room temperature for 5 h. The reaction mixture was partitioned between ethylacetate and water, organic layer dried over sodium sulphate ($Na_2SO_4$), filtered and concentrated. The residue was purified by silica gel flash chromatography to give subtitled compound (12 mg).

APCI-MS: m/z 204 (MH+). $^1$H-NMR (CDCl$_3$, 400 MHz): δ 8.48 (br.s, 1H); 7.18 (d, J=7.9 Hz, 1H); 6.97 (t, J=7.8 Hz,

1H); 6.60 (d, J=7.7 Hz, 1H); 6.22 (d, J=1.1 Hz, 1H); 4.45 (dd, J=2.8, 11.3 Hz, 1H); 4.10 (dd, J=5.9, 11.3 Hz, 1H); 2.97 (t, J=4.8 Hz, 1H); 2.83 (dd, J=2.8, 4.8 Hz, 1H); 2.43 (s, 3H).

(v) 5-Fluoro-1-(1-{(2S)-2-hydroxy-3-[(2-methyl-1H-indol-7-yl)oxy]propyl}4-piperidinyl)-1,3-dihydro-2H-benzimidazol-2-one A mixture of 5-fluoro-1-(4-piperidinyl)-1,3-dihydro-2H-benzimidazol-2-one (13.7 mg, 0.058 mmol), 2-methyl-7-[(2S)-oxiranylmethoxy]-1H-indole (12 mg, 0.058 mmol) in ethanol (2 mL) was kept on stirring at 80° C. for 5 h. The volatiles were removed in vacuo and residue purified by silica gel flash chromatography to give titled compound (18 mg).

$^1$H-NMR (CD$_3$OD, 400 MHz): δ 7.32 (dd, J=4.4, 8.7 Hz, 1H); 7.02 (d, J=7.9 Hz, 1H); 6.89-6.74 (m, 3H); 6.58 (d, J=7.6 Hz, 1H); 6.00 (s, 1H); 4.30 (m, 2H); 4.16 (dd, J=4.3, 9.9 Hz, 1H); 4.09 (dd, J=5.7, 9.9 Hz, 1H); 3.35 (s, 3H); 3.25 (m, 1H); 2.80 (m, 2H); 2.62-2.31 (m, 5H); 1.78 (m, 2H). APCI-MS: m/z 439 (MH$^+$).

EXAMPLE 40

5-Fluoro-1-(1-{(2S)-2-hydroxy-3-[(6-methoxy-2-methyl-1,3-benzoxazol-4-yl)oxy]propyl}-4-piperidinyl)-1,3-dihydro-2H-benzimidazol-2-one trifluoroacetate i) N-(2,6-Dihydroxy-4-methoxyphenyl)acetamide 2,6-Dihydroxy-4-methoxynitrobenzene (0.60 g, 3.24 mmol) was hydrogenated in the presence of acetic anhydride (0.29 g, 4.86 mmol) and 10% Pd/C (0.2 g) in methanol (30 mL) under atmospheric pressure and room temperature. The catalyst was removed by filtration through a pad of celite and the the crude product was purified by flash chromatography (SiO2, Toluene-ethyl acetate, 3:3 then 1:2) to afford the subtitle compound (0.43 g, 67.9%).

APCI-MS: m/z 198 (MH$^+$).

ii) 6-Methoxy-2-methyl-1,3-benzoxazol-4-ol 2,6-Dihydroxy-4-methoxynitrobenzene (0.27 g, 1.12 mmol) was heated to 200° C. in a closed vial for 30 min. The dark crude product was purified by flash chromatography (SiO2, heptane-ethyl acetate, 3:1 then 1:1) to afford the subtitle compound (112 mg, 56%).

APCI-MS: m/z 180 (MH$^+$).

iii) 6-Methoxy-2-methyl-1,3-benzoxazol-4-yl (2S)oxiranylmethyl ether

A suspension of 6-methoxy-2-methyl-1,3-benzoxazol-4-ol (0.11 g, 0.60 mmol), (2S)-2-[(3-nitrophenoxy)methyl] oxirane (0.16 g, 0.79 mmol) and cesium carbonate (0.44 g, 1.37 mmol) in dry DMF (4 mL) was stirred at room temperature for 5 hours. After aqueous work-up the crude product was purified by flash chromatography (SiO$_2$, toluene-ethyl acetate, 3:1) to afford the subtitle compound (0.118 g, 83.7%).

APCI-MS: m/z 236 (MH$^+$).

iv) 5-Fluoro-1-(1-{(2S)-2-hydroxy-3-[(6-methoxy-2-methyl-1,3-benzoxazol-4-yl)oxy]propyl}-4-piperidinyl)-1,3-dihydro-2H-benzimidazol-2-one trifluoroacetate The title compound was prepared from 6-methoxy-2-methyl-1,3-benzoxazol-4-yl (2S)oxiranylmethyl ether and 5-fluoro-1-(4-piperidinyl)-1,3-dihydro-2H-benzimidazol-2-one (prep. in analogy to Ex1i)) following the general procedure in Example 39 v).

$^1$H-NMR (CD$_3$OD, 400 MHz): δ7.26 (m, 1H), 6.82-6.88 (m, 3H), 6.53 (d, 1H, J=1.9 Hz), 4.47-4.62 (m, 2H), 4.21 (d, 2H, J=5.0 Hz), 3.3.87-3.94 (m, 2H), 3.84 (s, 3H), 3.48-350 (m, 2H), 2.84-2.97 (m, 2H), 2.60 (s, 3H), 2.09-2.16 (m, 2H). APCI-MS: m/z 471 (MH$^+$).

EXAMPLE 41

5-Fluoro-1-(1-{(2S)-2-hydroxy-3-[(6-hydroxy-2-methyl-1,3-benzoxazol-4-yl)oxy]propyl}piperidinyl-1,3-dihydro-2H-benzimidazol-2-one trifluoroacetate A cold (0° C.), stirred solution of 5-fluoro-1-(1-{(2S)-2-hydroxy-3-[(6-methoxy-2-methyl-1,3-benzoxazol-4-yl) oxy]propyl}-4-piperidinyl)-1,3-dihydro-2H-benzimidazol-2-one trifluoroacetate (prep. in analogy to Ex1i)) (66 mg, 0.11 mmol) in dry dichloromethane (10 mL) was treated with a 1M solution of boron tribromide in dichloromethane (0.68 mL) and the suspension was allowed to attain room temperature overnight. Methanol (4 mL) was added and the clear solution was concentrated under reduced temperature. The title compound was purified by HPLC.

APCI-MS: m/z 471 (MH$^+$).

EXAMPLE 42

N-[5-Bromo-2-({(2S)-3-[4-(5-fluoro-2-oxo-2,3-dihydro-1H-benzimidazol-1-yl)-1-piperidinyl]-2-hydroxypropyl}oxy)-4-methoxyphenyl]acetamide To a stirred suspension of N-[2-({(2S)-3-[4-(5-fluoro-2-oxo-2,3-dihydro-1H-benzimidazol-1-yl)-1-piperidinyl]-2-hydroxypropyl}oxy)-4-methoxyphenyl]acetamide (Example 32 iii)) (0.17 g, 0.36 mmol) in CH$_2$Cl$_2$ (5 ml) with some drops of DMF a solution of boron tribromide (BBr$_3$) in dichloromethane (CH$_2$Cl$_2$) (1M, 1.08 mmol, 1.08 ml) was added dropwise under nitrogen. The stirring was continued overnight art room temperature. Then the reaction mixture was quenched with methanol, diluted with water and extracted with dichloromethane (CH$_2$Cl$_2$) (2×10 ml) and ethyl acetate (2×10 ml). The combined organic extracts were dried with sodium sulphate and concentrated in vacuo. The residue was purified by flash chromatography of silica gel (CH$_2$Cl$_2$/MeOH, 9:1) to give a colourless solid (89 mg, 0.16 mmol, 45%).

APCI-MS: m/z 551 [MH$^+$]. $^1$H-NMR (400 MHz, DMSO-d$_6$): δ 11.01 (br. s, 1H), 9.18 (s, 1H), 7.76 (d, 1H, J=8.9), 7.20 (m, 1H), 6.7-6.9 (m, 3H), 5.05 (br. s, 1H), 4.0-4.2 (m, 3H), 3.9 (m, 1H), 3.73 (s, 3H), 3.08 (m, 1H), 3.01 (m, 1H), 2.54 (s, 2H), 2.1-2.5 (m, 5H), 2.06 (s, 3H), 1.62 (m, 2H),

EXAMPLE 43

N-Cyclopropyl-4-fluoro-2-({(2S)-3-[4-(5-fluoro-2-oxo-2,3-dihydro-1H-benzimidazol-1-yl)-1-piperidinyl]-2-hydroxypropyl}oxy)benzamide trifluoroaceate i) N-Cyclopropyl-4-fluoro-2-[(2S)oxiranylmethoxy]benzamide A mixture of methyl 4-fluoro-2-hydroxybenzoate (0.17 g, 1 mmol) and cyclopropylamine (1 ml) was stirred at room temperature overnight. Cyclopropylamine was removed in vacuo, and the residue dissolved in dry DMF (5 ml). (2S)-2-[(3-nitrophenoxy)-methyl]oxirane (0.195 g, 1.0 mmol) and cesium carbonate (0.478 g, 1.5 mmol) were added, and the mixture was stirred at room temperature for 2 days. The reaction mixture was partitioned between ethyl acetate (50 ml) and water (50 ml). The aqueous layer was extracted with ethyl acetate (25 ml) and the combined organic layers were dried with sodium sulphate and concentrated. The residue was purified by flash chromatography (silica gel, n-heptane/ethyl acetate, 1:1) to afford the subtitle compound (0.104 g, 0.41 mmol, 41%) as a colourless solid.

APCI-MS: m/z 252 [MH$^+$]. $^1$H-NMR (400 MHz, CDCl$_3$): δ 8.23 (dd, 1H), 7.81 (br.s, 1H), 6.80 (m, 1H), 6.63 (dd, 1H), 4.42 (dd, 1H), 4.03 (dd, 1H), 3.39 (m, 1H), 2.98 (mt, 2H), 2.82 (dd, 1H), 0.85 (m, 2H), 0.64 (m, 2H).

ii) N-Cyclopropyl-4-fluoro-2-({(2S)-3-[4-(5-fluoro-2-oxo-2,3-dihydro-1H-benzimidazol-1-yl)-1-piperidinyl]-2-hydroxypropyl}oxy)benzamide trifluoroaceate The tide compound was prepared according to the procedure described in Example 30 iii) from 5-fluoro-1-(4-piperidinyl)-1,3-dihydro-2H-benzimidazol-2-one and N-cyclopropyl-4-fluoro-2-[(2S)oxiranylmethoxy]benzamide. Yield 61%.

APCI-MS: m/z 487 [MH$^+$]. $^1$H-NMR (400 MHz, DMSO-d$_6$): δ 11.08 (s, 1H), 8.22 (s, 1H), 7.79 (m, 1H), 7.31 (br. s., 1H), 7.09 (m, 1H), 6.8-7.0 (m, 3H), 4.0-4.6 (m, 5H), 3.5-3.8 (m, 2H), 2.4-3.3 (m, 6H), 1.85 (m, 2H), 0.71 (m, 2H), 0.55 (M, 2H).

EXAMPLE 44

N-[2-({(2S)-3-[4-(5-Fluoro-2-oxo-2,3-dihydro-1H-benzimidazol-1-yl)-1-piperidinyl]-2-hydroxypropyl}oxy)-4-hydroxyphenyl]acetamide N-[2-({(2S)-3-[4-(5-Fluoro-2-oxo-2,3-dihydro-1H-benzimidazol-1-yl)-1-piperidinyl]-2-hydroxypropyl}oxy)-4-methoxyphenyl]acetamide, obtained in Example 32iii), (300 mg, 0.6 mmol) was dissolved in dichloromethane (5 ml) and stirred under nitrogen (N$_2$) at ambient (20-22° C.) temperature. Boron tribromide solution (1 M in dichloromethane, 2 ml, 2 mmol) was added dropwise. After stirring at ambient temperature for 17 hr dichloromethane (5 ml) and water (5 ml) were added. After 1 hr the solvent was removed in vacuo. The residue was purified by gradient flash chromatography on silica gel (CH$_2$Cl$_2$/MeOH, 100/0 to 70/30) and lyophilized yielding the title compound as a white solid (134 mg, 49%).

APCI-MS: m/z 459 [MH$^+$]. $^1$H-NMR (400 MHz, MeOH-d$_4$) δ: 7.42 (dd, 2H, J=8.6, J=2.6); 6.8-6.9 (m, 2H); 6.52 (d, 1H, J=2.4); 6.40 (dd, 1H, J=8.6, J=2.5); 4.6-4.7 (m, 1H); 4.5-4.6 (m, 1H); 4.05 (d, 2H, J=5.1); 3.90 (br.d, 2H, J=11.9); 3.4-3.5 (m, 4H); 2.8-3.0 (m, 2H); 2.19 (s, 3H); 2.10 (br.t, 2H, J=13.3)

EXAMPLE 45

N-[5-Bromo-2-({(2S)-3-[4-(5-fluoro-2-oxo-2,3-dihydro-1H-benzimidazol-1-yl)1-piperidinyl]-2-hydroxypropyl}oxy)-4-hydroxyphenyl]acetamide Starting from N-[5-bromo-2-({(2S)-3-[4-(5-fluoro-2-oxo-2,3-dihydro-1H-benzimidazol-1-yl)-1-piperidinyl]-2-hydroxypropyl}oxy)-4-methoxyphenyl]acetamide the tide compound was prepared by analogy to Example 44. Purification using HPLC (Kromasil C18-column, acetonitrile/H$_2$O/0.1% TFA) afforded a white solid (14 mg, 20%).

APCI-MS: m/z 538 [MH$^+$]. $^1$H-NMR (400 MHz, MeOH-d$_4$) δ: 7.78 (s, 1H); 7.2-7.3 (m, 1H); 6.8-6.9 (m, 2H); 6.64 (s, 1H); 4.5-4.6 (m, 1H); 4.4-4.5 (m, 1H); 4.04 (d, 2H, J=4.6); 3.86 (br.t, 2H, J=12.3); 3.2-3.4 (m, 2H); 3.38 (d, 2H, J=6.7); 2.8-3.0 (m, 2H); 2.16 (s, 3H); 2.12 (br.t, 2H, J=14.6)

EXAMPLE 46

N-[4,5-Difluoro-2-({(2S)-3-[4-(5-fluoro-2-oxo-2,3-dihydro-1H-benzimidazol-1-yl)-1-piperidinyl]-2-hydroxypropyl}oxy)phenyl]acetamide i) 4,5-Difluoro-2-nitro-phenol 3,4-Difluorophenol (3.10 g, 23.7 mmole) was dissolved in acetic acid (15 ml). To the stirred solution was added dropwise a solution of fuming nitric acid (HNO$_3$) (1.25 g, 29.7 mmole) in acetic acid (6 ml). The temperature was kept under 50° C. during the entire addition. After completed addition, the mixture was stirred for another hour. The reaction mixture was poured onto ice-water, giving precipitation of a yellowish solid.

The solid was collected by filtration, and dried. The solid was purified on silica (Heptane: Ethyl acetate (EtOAc) 5:1), giving the sub-title compound (2.05 g, 50%) as a yellow oil, which crystallized on standing.

$^1$H-NMR (400 MHz, CDCl$_3$) δ: 10.61 (1H, s); 8.00 (1H, dd, J 9.6 8.2 Hz); 7.00 (1H, dd, J 10.4 6.8 Hz)

ii) N-(4,5-Difluoro-2-hydroxy-phenyl)-acetamide

In a flask was added the product obtained in i) (0.59 g, 3.37 mmole), and acetic acid (10 ml). The solution was heated with stirring to 90° C., and tin (powder, 1.60 g, 13.5 mmole) was added. The flask was sealed and heated with stirring for another hour, and the hot solution was filtered through celite. The filter was then washed with another 10 ml of hot acetic acid. To the filtrate was added water (25 ml) and acetic anhydride (0.5 ml, 5.29 mmole), and the resulting mixture was heated with stirring at 60° C. for 20 minutes. The mixture was allowed to cool, and was partitioned between ethyl acetate (EtOAc) and water. The organic phase was collected and washed with water and brine. The organic phase was evaporated to give the 0.63 g (100%) of the sub-title compound as a solid.

$^1$H-NMR (400 MHz, DMSO-d$_6$) δ: 10.25 (1H, s); 9.31 (1H, bs); 7.88 (1H, dd, J 12.8 7.9 Hz); 6.83 (1H, dd, J 12.1 7.7 Hz); 2.08 (3H, s)

iii) N-(4,5-Difluoro-2-oxiranylmethoxy-phenyl)-acetamide

The product obtained in ii) (182 mg, 0.97 mmol) and (2R)oxiranylmethyl-3-nitrobenzenesulfonate (221 mg, 1.18 mmol) were dissolved in dry dimethylformamide (1 ml). Potassium carbonate (295 mg, 2.1 mmol) was added. The resulting turbid solution was stirred under nitrogen ($N_2$) at ambient temperature for 17 hrs. Water (2 ml) and ethyl is acetate (2 ml) was added, and the layers were separated. The organic layer was washed several times with water, dried ($MgSO_4$) and evaporated. The crude product was purified on HPLC (Kromasil C18-column, acetonitrile/$H_2O$).

APCI-MS: m/z 244 [MH$^+$]

iv) N-[4,5-Difluoro-2-({(2S)-3-[4-(5-fluoro-2-oxo-2,3-dihydro-1H-benzimidazol-1-yl)-1-piperidinyl]-2-hydroxypropyl}oxy)phenyl]acetamide The product obtained in iii) (10 mg, 0.04 mmol) and 5-fluoro-1-(4-piperidinyl)-1,3-dihydro-2H-benzimidazol-2-one (prep. in analogy to Ex1i)) (12.3 mg, 0.05 mmol), were dissolved in 2-propanol (1 ml), and stirred at 90° C. for 4 hrs. The solvent was evaporated and the crude product was purified on HPLC (Kromasil C18-column, acetonitrile/$H_2O$/0.1% TFA). Finally lyophilization afforded the title compound as a white solid (15 mg, 75%).

APCI-MS: m/z 479 [MH$^+$]$^1$H-NMR (400 MHz, MeOH-$d_4$) δ: 7.9-8.0 (m, 1H); 7.3-7.4 (m, 1H); 7.07 (dd, 1H, J=11.9, J=7.3); 6.8-6.9 (m, 2H); 4.5-4.6 (m, 1H); 4.4-4.5 (m, 1H); 4.0-4.1 (m, 2H); 3.89 (br.d, 2H, J=11.4); 3.41 (d, 2H, J=7.9); 3.2-3.5 (m, 2H); 2.8-3.0 (m, 2H); 2.19 (s, 3H); 2.11 (br.t, 2H, J=13.5)

EXAMPLE 47

N-[5-Fluoro-2-({(2S)-3-[4-(5-fluoro-2-oxo-2,3-dihydro-1H-benzimidazol-1-yl)-1-piperidinyl]-2-hydroxypropyl}oxy)phenyl]acetamide i) N-(5-Fluoro-2-hydroxyphenyl)-acetamide

Starting from the commercially available 5-fluoro-2-nitro-phenol the sub-title compound was prepared by analogy to Example 46ii).

ii) N-{5-Fluoro-2-[(2S)oxiranylmethoxy]phenyl}acetamide

Starting from the product obtained in i) the sub-title compound was prepared by analogy to Example 46iii).

APCI-MS: m/z 226 [MH$^+$]

iii) N-[5-Fluoro-2-({(2S)-3-[4-(5-fluoro-2-oxo-2,3-dihydro-1H-benzimidazol-1-yl)-1-piperidinyl]-2-hydroxypropyl}oxy)phenyl]acetamide Starting from the product obtained in ii) the title compound was prepared by analogy to Example 46iv). Purification using HPLC (Kromasil C18-column, acetonitrile/$H_2O$/0.1% TFA) afforded the title compound as a white solid (107 mg, 69%).

APCI-MS: m/z 461 [MH$^+$]$^1$H-NMR (300 MHz, MeOH-$d_4$) δ: 7.88 (dd, 1H, J=10.6, J=3.2); 7.2-7.3 (m, 1H); 7.0-7.1 (m, 1H); 6.8-6.9 (m, 3H); 4.5-4.6 (m, 1H); 4.4-4.5 (m, 1H); 4.08 (d, 2H, J=4.1); 3.88 (br.t, 2H, J=9.9); 3.42 (d, 2H, J=8.6); 3.2-3.5 (m, 2H); 2.8-3.0 (m, 2H); 2.21 (s, 3H); 2.11 (br.t, 2H, J=11.9)

THP-1 Chemotaxis Assay

Introduction

The assay measured the chemotactic response elicited by MIP-1α chemokine in the human monocytic cell line THP-1. The compounds of the Examples were evaluated by their ability to depress the chemotactic response to a standard concentration of MIP-1α chemokine.

Methods

Culture of THP-1 Cells

Cells were thawed rapidly at 37° C. from frozen aliquots and resuspended in a 25 cm flask containing 5 ml of RPMI-1640 medium supplemented with Glutamax and 10% heat inactivated fetal calf serum without antibiotics (RPMI+10% HIFCS). At day 3 the medium is discarded and replaced with fresh medium.

THP-1 cells are routinely cultured in RPMI-1640 medium supplemented with 10% heat inactivated fetal calf serum and glutamax but without antibiotics. Optimal growth of the cells requires that they are passaged every 3 days and that the minimum subculture density is 4×10+5 cells/ml.

Chemotaxis Assay

Cells were removed from the flask and washed by centrifugation in RPMI+10% HIFCS+glutamax. The cells were then resuspended at 2×10+7 cells/ml in fresh medium (RPMI+10% HIFCS+glutamax) to which was added calcein-AM (5 μl of stock solution to 1 ml to give a final concentration of 5×10$^{-6}$M). After gentle mixing the cells were incubated at 37° C. in a $CO_2$ incubator for 30 minutes. The cells were then diluted to 50 ml with medium and washed twice by centrifugation at 400×g. Labelled cells were then resuspended at a cell concentration of 1×10+7 cells/ml and incubated with an equal volume of MIP-1α antagonist (10$^{-10}$M to 10$^{-6}$M final concentration) for 30 minutes at 37° C. in a humidified $CO_2$ incubator.

Chemotaxis was performed using Neuroprobe 96-well chemotaxis plates employing 8 μm filters (cat no. 101-8). Thirty microliters of chemoattractant supplemented with various concentrations of antagonists or vehicle were added to the lower wells of the plate in triplicate. The filter was then carefully positioned on top and then 25 μl of cells preincubated with the corresponding concentration of antagonist or vehicle were added to the surface of the filter. The plate was then incubated for 2 hours at 37° C. in a humidified $CO_2$ incubator. The cells remaining on the surface were then removed by adsorption and the whole plate was centrifuged at 2000 rpm for 10 minutes. The filter was then removed and the cells that had migrated to the lower wells were quantified by the fluorescence of cell associated calcein-AM. Cell migration was then expressed in fluorescence units after subtraction of the reagent blank and values were standardized to % migration by comparing the fluorescence values with that of a known number of labelled cells. The effect of antagonists was calculated as % inhibition when the number of migrated cells were compared with vehicle.

What is claimed is:

1. A compound of formula

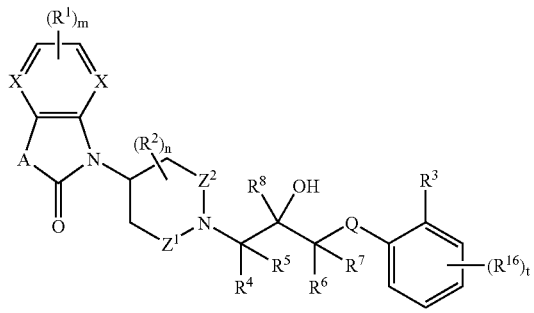

(I)

wherein
A represents an oxygen atom or a group NH;
each X represents a group CH;
m is 0, 1, 2, 3 or 4;
each $R^1$ independently represents halogen, cyano, nitro, carboxyl, hydroxyl, $C_1$-$C_6$ alkyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^9R^{10}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsulphonyl or —$C(O)NR^{11}R^{12}$;
n is 0, 1 or 2;
each $R^2$ independently represents a $C_1$-$C_6$ alkyl, $C_1$-$C_6$ alkoxycarbonyl, —$CH_2OH$ or carboxyl group;
$Z^1$ represents a group $(CH_2)_q$ where q is 1; $Z^2$ represents a group $CH_2$;
or $Z^1$ represents a group $(CH_2)_q$ where q is 2; $Z^2$ represents a bond;
Q represents an oxygen or sulphur atom or a group $CH_2$ or NH;
$R^3$ represents —$NHC(O)R^{13}$, —$C(O)NR^{14}R^{15}$, —NH—$R^{15a}$ or —O—$R^{15b}$, or
$R^3$ together with the six-membered ring to which it is attached forms a group of formula

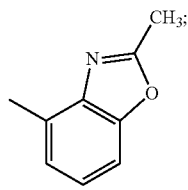

$R^4$, $R^5$, $R^6$ and $R^7$ each independently represent a hydrogen atom or a $C_1$-$C_6$ alkyl group, or $R^4$, $R^5$, $R^6$ and $R^7$ together represent a $C_1$-$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;
$R^8$ represents a hydrogen atom, a $C_1$-$C_6$ alkyl group or is linked to $R^4$ as defined above;
$R^9$ and $R^{10}$ each independently represent a hydrogen atom or a $C_1$-$C_6$ alkyl group, or $R^9$ and $R^{10}$ together with the nitrogen atom to which they are attached form a 4- to 7-membered saturated heterocycle;
$R^{11}$ and $R^{12}$ each independently represent a hydrogen atom or a $C_1$-$C_6$ alkyl group;
$R^{13}$ represents a group $C_2$-$C_6$ alkenyl, $C_3$-$C_6$ cycloalkyl, adamantyl, $C_5$-$C_6$ cycloalkenyl, phenyl or a saturated or unsaturated 5- to 10-membered heterocyclic ring system having at least one ring heteroatom selected from nitrogen, oxygen and sulphur, each of which may be optionally substituted by one or more substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —$NHC(O)$—$R^{17}$;
$R^{14}$ and $R^{15}$ each independently represent (i) a hydrogen atom, (ii) a 3- to 6-membered saturated or unsaturated ring optionally having at least one ring heteroatom selected from nitrogen, oxygen and sulphur, the ring being optionally substituted with at least one substituent selected from hydroxyl, halogen, methyl, methoxy and trifluoromethyl, or
(iii) a $C_1$-$C_6$ alkyl group optionally substituted by at least one substituent selected from halogen, trifluoromethyl, carboxyl, $C_1$-$C_6$ alkoxycarbonyl and a 5- to 6-membered saturated or unsaturated ring optionally having at least one ring heteroatom selected from nitrogen, oxygen and sulphur, the ring being optionally substituted with at least one substituent selected from halogen, methyl and trifluoromethyl, or
$R^{14}$ and $R^{15}$ together with the nitrogen atom to which they are attached form a 4- to 7-membered saturated heterocycle;
$R^{15a}$ and $R^{15b}$ each independently represent a 5- to 6-membered saturated or unsaturated heterocyclic ring having at least one ring heteroatom selected from nitrogen, oxygen and sulphur, the ring being optionally substituted with at least one substituent selected from halogen, methyl and trifluoromethyl;
t is 0, 1, 2 or 3;
each $R^{16}$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^{18}R^{19}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsulphonyl, —$C(O)NR^{20}R^{21}$, —$NR^{22}C(O)(NH)_vR^{23}$, phenyl, or $C_1$-$C_6$ alkyl optionally substituted by at least one substituent selected from carboxyl and $C_1$-$C_6$ alkoxycarbonyl;
$R^{17}$ represents a $C_1$-$C_6$ alkyl, amino or phenyl group;
$R^{18}$ and $R^{19}$ each independently represent a hydrogen atom or a $C_1$-$C_6$ alkyl group, or $R^{18}$ and $R^{19}$ together with the nitrogen atom to which they are attached form a 4- to 7-membered saturated heterocycle;
$R^{20}$ and $R^{21}$ each independently represent a hydrogen atom or a $C_1$-$C_6$ alkyl group optionally substituted by $C_1$-$C_6$ alkoxycarbonyl;
v is 0 or 1;
$R^{22}$ represents a hydrogen atom or a $C_1$-$C_6$ alkyl group; and
$R^{23}$ represents a hydrogen atom, or a $C_1$-$C_6$ alkyl group optionally substituted by at least one substituent selected from carboxyl, $C_1$-$C_6$ alkoxy and $C_1$-$C_6$ alkoxycarbonyl;
or a pharmaceutically acceptable salt.

2. A compound according to claim 1, wherein A represents NH.

3. A compound according to claim 1, wherein each $R^1$ independently represents halogen or $C_1$-$C_6$ haloalkyl.

4. A compound according to claim 1, wherein $Z^1$ and $Z^2$ both represent $CH_2$.

5. A compound according to claim 1, wherein $R^4$, $R^5$, $R^6$, $R^7$ and $R^8$ each independently represent a hydrogen atom or a $C_1$-$C_6$ alkyl group.

6. A compound according to claim 1, wherein $R^3$ represents —NHC(O)$R^{13}$ in which $R^{13}$ represents a group phenyl or a saturated or unsaturated 5- to 6-membered heterocyclic ring system having at least one ring heteroatom selected from nitrogen, oxygen and sulphur, each of which may be optionally substituted by one, two, three or four substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —NHC(O)—$R^{17}$; or $R^3$ represents —C(O)N$R^{14}R^{15}$ in which $R^{14}$ and $R^{15}$ each independently represent (i) a hydrogen atom, (ii) a 3- to 6-membered saturated or unsaturated ring optionally having at least one ring heteroatom selected from nitrogen, oxygen and sulphur, the ring being optionally substituted with at least one substituent selected from halogen, methyl, methoxy and trifluoromethyl, or (iii) a $C_1$-$C_6$ alkyl group.

7. A compound according to claim 1 being:

N-(2-{2-Hydroxy-2-methyl-3-[4-(2-oxo-2,3-dihydro-1H-benzimidazol-1-yl)-1-piperidinyl]propoxy}phenyl)-2-pyridinecarboxamide, or N-(2-{2-Hydroxy-3-[4-(2-oxo-2,3-dihydro-1H-benzimidazol-1-yl)-1-piperidinyl]propoxy}phenyl)benzamide hydrochloride, or 2-{2-Hydroxy-3-[4-(2-oxo-2,3-dihydro-1H-benzimidazol-1-yl)-1-piperidinyl]propoxy}-N-methylbenzamide, or N-(2-{3-[4-(6-Chloro-2-oxo-2,3-dihydro-1H-benzimidazol-1-yl)-1-piperidinyl]-2-hydroxypropoxy}phenyl)-4-methylbenzamide, or 4-Chloro-N-[2-(2-hydroxy-3-{4-[2-oxo-5-(trifluoromethyl)-2,3-dihydro-1H-benzimidazol-1-yl]-1-piperidinyl}propoxy)phenyl]benzamide, or N-(2-{3-[4-(5-Fluoro-2-oxo-2,3-dihydro-1H-benzimidazol-1-yl)-1-piperidinyl]-2-hydroxypropoxy}phenyl)benzamide, or N-(2-{3-[4-(5-Fluoro-2-oxo-2,3-dihydro-1H-benzimidazol-1-yl)-1-piperidinyl]-2-hydroxypropoxy}phenyl)-4-methoxybenzamide, or N-[2-(2-Hydroxy-3-{4-[2-oxo-5-(trifluoromethyl)-2,3-dihydro-1H-benzimidazol-1-yl]-1-piperidinyl}propoxy)phenyl]benzamide, or 4-Chloro-N-(2-{3-[4-(6-chloro-2-oxo-2,3-dihydro-1H-benzimidazol-1-yl)-1-piperidinyl]-2-hydroxypropoxy}phenyl)benzamide, or N-(2-{2-Hydroxy-3-[4-(2-oxo-1,3-benzoxazol-3(2H)-yl)-1-piperidinyl]propoxy}phenyl)-4-methylbenzamide, or 4-Chloro-N-(2-{3-[4-(5-fluoro-2-oxo-2,3-dihydro-1H-benzimidazol-1-yl)-1-piperidinyl]-2-hydroxypropoxy}phenyl)benzamide, or N-(2-{2-Hydroxy-3-[4-(2-oxo-1,3-benzoxazol-3(2H)-yl)-1-piperidinyl]propoxy}phenyl)benzamide, or N-(2-{3-[4-(5-Fluoro-2-oxo-2,3-dihydro-1H-benzimidazol-1-yl)-1-piperidinyl]-2-hydroxypropoxy}phenyl)-4-methylbenzamide, or 4-Chloro-N-(2-{2-hydroxy-3-[4-(2-oxo-1,3-benzoxazol-3(2H)-yl)-1-piperidinyl]propoxy}phenyl)benzamide, or 4-Chloro-N-(2-{2-hydroxy-3-[4-(2-oxo-2,3-dihydro-1H-benzimidazol-1-yl)-1-piperidinyl]propoxy}phenyl)benzamide, or N-(2-{2-Hydroxy-2-methyl-3-[4-(2-oxo-2,3-dihydro-1H-benzimidazol-1-yl)-1-piperidinyl]propoxy}phenyl)benzamide, or N-(2-{3-[4-(5-Fluoro-2-oxo-2,3-dihydro-1H-benzimidazol-1-yl)-1-piperidinyl]-2-hydroxypropoxy}phenyl)-5-isoxazolecarboxamide, or N-(2-{2-Hydroxy-3-[4-(2-oxo-2,3-dihydro-1H-benzimidazol-1-yl)-1-piperidinyl]propoxy}phenyl)-4-methylbenzamide, or 2-{3-[4-(5-Fluoro-2-oxo-2,3-dihydro-1H-benzimidazol-1-yl)-1-piperidinyl]-2-hydroxypropoxy}-N-methylbenzamide, or 5-Fluoro-1-(1-{(2S)-2-hydroxy-3-[(2-methyl-1,3-benzoxazol-4-yl)oxy]propyl}-4-piperidinyl)-1,3-dihydro-2H-benzimidazol-2-one trifluoroacetate, or 2-{3-[4-(5-Fluoro-2-oxo-2,3-dihydro-benzoimidazol-1-yl)piperidin-1-yl]-2-hydroxy-propoxy}-N-cyclopropyl-benzamide, or 2-{3-[4-(5-Fluoro-2-oxo-2,3-dihydro-benzoimidazol-1-yl)piperidin-1-yl]-2-hydroxy-propoxy}-N-(3-hydroxy-pyridin-2-yl)-benzamide, or 2-({(2S)-3-[4-(5-Chloro-2-oxo-2,3-dihydro-1H-benzimidazol-1-yl)-1-piperidinyl]-2-hydroxypropyl}-N-cyclopropylbenzamide(trifluoroacetate), or 5-Fluoro-1-(1-{(2S)-2-hydroxy-3-[(6-methoxy-2-methyl-1,3-benzoxazol-4-yl)oxy]propyl}-4-piperidinyl)-1,3-dihydro-2H-benzimidazol-2-one trifluoroacetate, or 5-Fluoro-1-(1-{(2S)-2-hydroxy-3-[(6-hydroxy-2-methyl-1,3-benzoxazol-4-yl)oxy]propyl}-4-piperidinyl)-1,3-dihydro-2H-benzimidazol-2-one trifluoroacetate, or N-Cyclopropyl-4-fluoro-2-({(2S)-3-[4-(5-fluoro-2-oxo-2,3-dihydro-1H-benzimidazol-1-yl)-1-piperidinyl]-2-hydroxypropyl}oxy)benzamide trifluoroaceate.

8. The compound of claim 1, wherein $R^3$ represents —NHC(O)$R^{13}$, —C(O)N$R^{14}R^{15}$, —NH—$R^{15a}$ or —O—$R^{15b}$, or $R^3$ together with the six-membered ring to which it is attached forms a group of formula

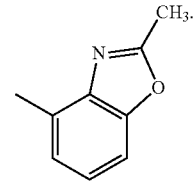

9. A process for the preparation of a compound of formula (I) as defined in claim 1 which comprises, (a) reacting a compound of formula

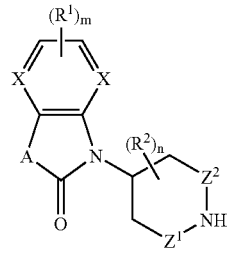

wherein A, X, m, $R^1$, n, $R^2$, $Z^1$ and $Z^2$ are as defined in formula (I), with a compound of formula (III)

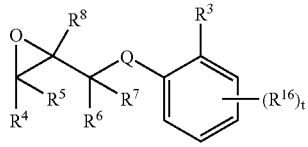

wherein Q, $R^3$, $R^4$, $R^5$, $R^6$, $R^7$, $R^8$, t and $R^{16}$ are as defined in formula (I); or (b) reacting a compound of formula (IV)

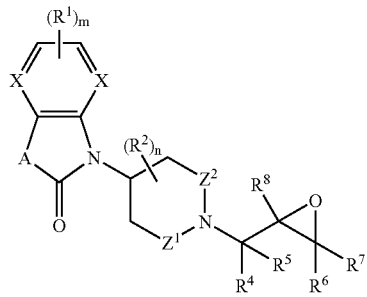

wherein A, X, m, $R^1$, n, $R^2$, $Z^1$, $Z^2$, $R^4$, $R^5$, $R^6$, $R^7$ and $R^8$ are as defined in formula (I), with a compound of formula (V)

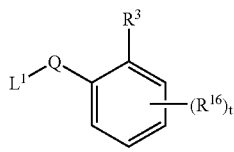

wherein $L^1$ represents a hydrogen atom or an activating group and Q, $R^3$, t and $R^{16}$ are as defined in formula (I); or (c) when $R^3$ represents —NHC(O)$R^{13}$, reacting a compound of formula (VI)

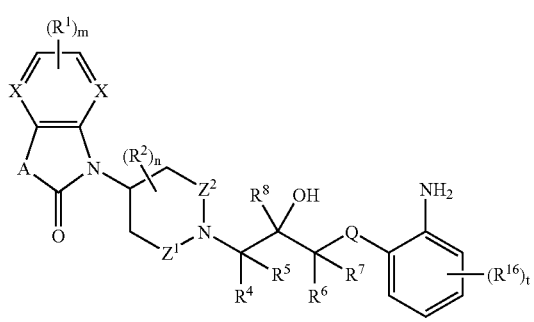

wherein A, X, m, $R^1$, n, $R^2$, $Z^1$, $Z^2$, $R^4$, $R^5$, $R^6$, $R^7$, $R^8$, Q, t and $R^{16}$ are as defined in formula (I), with a compound of formula (VII)

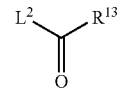

wherein $L^2$ represents a leaving group and $R^{13}$ is as defined in formula (I); or (d) when $R^3$ represents —C(O)NR$^{14}$R$^{15}$, reacting a compound of formula (VIII)

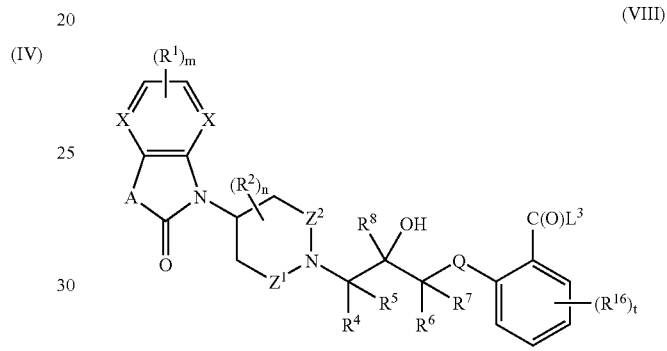

wherein $L^3$ represents a leaving group and A, X, m, $R^1$, n, $R^2$, $Z^1$, $Z^2$, $R^4$, $R^5$, $R^6$, $R^7$, $R^8$, Q, t and $R^{16}$ are as defined in formula (I), with a compound of formula (IX), NHR$^{14}$R$^{15}$, wherein $R^{14}$ and $R^{15}$ are as defined in formula (I);

and optionally after (a), (b), (c) or (d) forming a pharmaceutically acceptable salt.

10. A pharmaceutical composition comprising an effective amount of a compound of formula (I), or a pharmaceutically acceptable salt, as claimed in claim 1 in association with a pharmaceutically acceptable adjuvant, diluent or carrier.

11. A process for the preparation of a pharmaceutical composition as claimed in claim 10 which comprises mixing a compound of formula (I), or a pharmaceutically acceptable salt, as claimed in claim 1 with a pharmaceutically acceptable adjuvant, diluent or carrier.

12. A method of treating rheumatoid arthritis which comprises administering to a patient in need thereof a therapeutically effective amount a compound of formula (I), or a pharmaceutically acceptable salt as claimed in claim 1.

13. A method of treating chronic obstructive pulmonary disease which comprises administering to a patient in need thereof a therapeutically effective amount a compound of formula (I), or a pharmaceutically acceptable salt as claimed in claim 1.

14. A method of treating asthma which comprises administering to a patient in need thereof a therapeutically effective amount of a compound of formula (I), or a pharmaceutically acceptable salt as claimed in claim 1.

15. A compound of formula

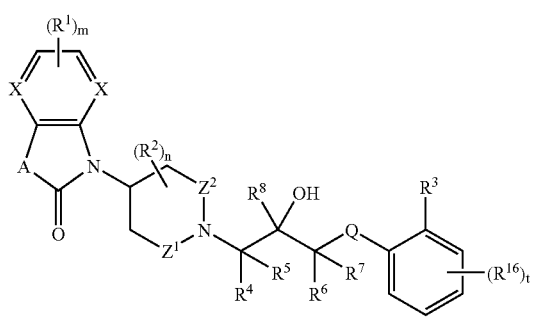

wherein
A represents an oxygen atom or a group NH;
each X represents a group CH;
m is 1;
each $R^1$ independently represents halogen, cyano, nitro, carboxyl, hydroxyl, $C_1$-$C_6$ alkyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^9R^{10}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsulphonyl or —$C(O)NR^{11}R^{12}$;
n is 0, 1 or 2;
each $R^2$ independently represents a $C_1$-$C_6$ alkyl, $C_1$-$C_6$ alkoxycarbonyl, —$CH_2OH$ or carboxyl group;
$Z^1$ represents a group $CH_2$; $Z^2$ represents $CH_2$; or $Z^1$ represents $(CH_2)_2$; $Z^2$ represents a bond;
Q represents an oxygen or sulphur atom or a group $CH_2$ or NH;
$R^3$ represents —$NHC(O)R^{13}$, —$C(O)NR^{14}R^{15}$, —NH—$R^{15a}$ or —O—$R^{15b}$, or
$R^3$ together with the six-membered ring to which it is attached forms a group of formula

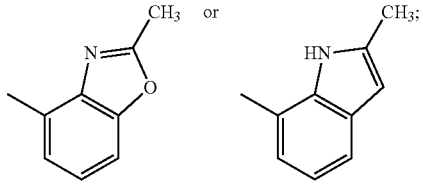

$R^4$, $R^5$, $R^6$ and $R^7$ each independently represent a hydrogen atom or a $C_1$-$C_6$ alkyl group, or $R^4$, $R^5$, $R^6$ and $R^7$ together represent a $C_1$-$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;
$R^8$ represents a hydrogen atom, a $C_1$-$C_6$ alkyl group or is linked to $R^4$ as defined above;
$R^9$ and $R^{10}$ each independently represent a hydrogen atom or a $C_1$-$C_6$ alkyl group, or $R^9$ and $R^{10}$ together with the nitrogen atom to which they are attached form a 4- to 7-membered saturated heterocycle;
$R^{11}$ and $R^{12}$ each independently represent a hydrogen atom or a $C_1$-$C_6$ alkyl group;

$R^{13}$ represents a group $C_1$-$C_6$ alkyl, $C_2$-$C_6$ alkenyl, $C_3$-$C_6$ cycloalkyl, adamantyl, $C_5$-$C_6$ cycloalkenyl, phenyl or a saturated or unsaturated 5- to 10-membered heterocyclic ring system having at least one ring heteroatom selected from nitrogen, oxygen and sulphur, each of which may be optionally substituted by one or more substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —NHC(O)—$R^{17}$;
$R^{14}$ and $R^{15}$ each independently represent (i) a hydrogen atom, (ii) a 3- to 6-membered saturated or unsaturated ring optionally having at least one ring heteroatom selected from nitrogen, oxygen and sulphur, the ring being optionally substituted with at least one substituent selected from hydroxyl, halogen, methyl, methoxy and trifluoromethyl, or
(iii) a $C_1$-$C_6$ alkyl group optionally substituted by at least one substituent selected from halogen, trifluoromethyl, carboxyl, $C_1$-$C_6$ alkoxycarbonyl and a 5- to 6-membered saturated or unsaturated ring optionally having at least one ring heteroatom selected from nitrogen, oxygen and sulphur, the ring being optionally substituted with at least one substituent selected from halogen, methyl and trifluoromethyl, or
$R^{14}$ and $R^{15}$ together with the nitrogen atom to which they are attached form a 4- to 7-membered saturated heterocycle;
$R^{15a}$ and $R^{15b}$ each independently represent a 5- to 6-membered saturated or unsaturated heterocyclic ring having at least one ring heteroatom selected from nitrogen, oxygen and sulphur, the ring being optionally substituted with at least one substituent selected from halogen, methyl and trifluoromethyl;
t is 0, 1, 2 or 3;
each $R^{16}$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^{18}R^{19}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsulphonyl, —$C(O)NR^{20}R^{21}$, —$NR^{22}C(O)(NH)_vR^{23}$, phenyl, or $C_1$-$C_6$ alkyl optionally substituted by at least one substituent selected from carboxyl and $C_1$-$C_6$ alkoxycarbonyl;
$R^{17}$ represents a $C_1$-$C_6$ alkyl, amino or phenyl group;
$R^{18}$ and $R^{19}$ each independently represent a hydrogen atom or a $C_1$-$C_6$ alkyl group, or $R^{18}$ and $R^{19}$ together with the nitrogen atom to which they are attached form a 4- to 7-membered saturated heterocycle;
$R^{20}$ and $R^{21}$ each independently represent a hydrogen atom or a $C_1$-$C_6$ alkyl group optionally substituted by $C_1$-$C_6$ alkoxycarbonyl;
v is 0 or 1;
$R^{22}$ represents a hydrogen atom or a $C_1$-$C_6$ alkyl group; and
$R^{23}$ represents a hydrogen atom, or a $C_1$-$C_6$ alkyl group optionally substituted by at least one substituent selected from carboxyl, $C_1$-$C_6$ alkoxy and $C_1$-$C_6$ alkoxycarbonyl;
or a pharmaceutically acceptable salt.

16. A compound according to claim 15, wherein A represents NH.

17. A compound according to claim 15, wherein each $R^1$ independently represents halogen or $C_1$-$C_6$ haloalkyl.

18. A compound according to claim 15, wherein $Z^1$ and $Z^2$ both represent $CH_2$.

19. A compound according to claim 15, wherein $R^4$, $R^5$, $R^6$, $R^7$ and $R^8$ each independently represent a hydrogen atom or a $C_1$-$C_6$ alkyl group.

20. A compound according to claim 15, wherein $R^3$ represents —NHC(O)$R^{13}$ in which $R^{13}$ represents a group $C_1$-$C_6$ alkyl, phenyl or a saturated or unsaturated 5- to 6-membered heterocyclic ring system having at least one ring heteroatom selected from nitrogen, oxygen and sulphur, each of which may be optionally substituted by one, two, three or four substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —NHC(O)—$R^{17}$; or $R^3$ represents —C(O)NR$^{14}$R$^{15}$ in which $R^{14}$ and $R^{15}$ each independently represent (i) a hydrogen atom, (ii) a 3- to 6-membered saturated or unsaturated ring optionally comprising having at least one ring heteroatom selected from nitrogen, oxygen and sulphur, the ring being optionally substituted with at least one substituent selected from halogen, methyl, methoxy and trifluoromethyl, or (iii) a $C_1$-$C_6$ alkyl group.

21. A compound according to claim 15 being:

N-[2-(2-Hydroxy-3-{4-[2-oxo-5-(trifluoromethyl)-2,3-dihydro-1H-benzimidazol-1-yl]-1-piperidinyl}propoxy)phenyl]acetamide, or N-(2-{3-[4-(6-Chloro-2-oxo-2,3-dihydro-1H-benzimidazol-1-yl)-1-piperidinyl]-2-hydroxypropoxy}phenyl)-4-methylbenzamide, or 4-Chloro-N-[2-(2-hydroxy-3-{4-[2-oxo-5-(trifluoromethyl)-2,3-dihydro-1H-benzimidazol-1-yl]-1-piperidinyl}propoxy)phenyl]benzamide, or N-[2-({(2R)-3-[4-(5-Fluoro-2-oxo-2,3-dihydro-1H-benzimidazol-1-yl)-1-piperidinyl]-2-hydroxypropyl}oxy)phenyl]acetamide hydrochloride, or N-(2-{3-[4-(5-Fluoro-2-oxo-2,3-dihydro-1H-benzimidazol-1-yl)-1-piperidinyl]-2-hydroxypropoxy}phenyl)benzamide, or N-[2-({(2S)-3-[4-(5-Fluoro-2-oxo-2,3-dihydro-1H-benzimidazol-1-yl)-1-piperidinyl]-2-hydroxypropyl}oxy)phenyl]acetamide hydrochloride, or N-(2-{3-[4-(5-Fluoro-2-oxo-2,3-dihydro-1H-benzimidazol-1-yl)-1-piperidinyl]-2-hydroxypropoxy}phenyl)acetamide, or N-(2-{3-[4-(6-Chloro-2-oxo-2,3-dihydro-1H-benzimidazol-1-yl)-1-piperidinyl]-2-hydroxypropoxy}phenyl)acetamide, or N-(2-{3-[4-(5-Fluoro-2-oxo-2,3-dihydro-1H-benzimidazol-1-yl)-1-piperidinyl]-2-hydroxypropoxy}phenyl)-4-methoxybenzamide, or N-[2-(2-Hydroxy-3-{4-[2-oxo-5-(trifluoromethyl)-2,3-dihydro-1H-benzimidazol-1-yl]-1-piperidinyl}propoxy)phenyl]benzamide, or 4-Chloro-N-(2-{3-[4-(6-chloro-2-oxo-2,3-dihydro-1H-benzimidazol-1-yl)-1-piperidinyl]-2-hydroxypropoxy}phenyl)benzamide, or 4-Chloro-N-(2-{3-[4-(5-fluoro-2-oxo-2,3-dihydro-1H-benzimidazol-1-yl)-1-piperidinyl]-2-hydroxypropoxy}phenyl)benzamide, or N-(2-{3-[4-(5-Fluoro-2-oxo-2,3-dihydro-1H-benzimidazol-1-yl)-1-piperidinyl]-2-hydroxypropoxy}phenyl)-4-methylbenzamide, or N-(2-{3-[4-(5-Fluoro-2-oxo-2,3-dihydro-1H-benzimidazol-1-yl)-1-piperidinyl]-2-hydroxypropoxy}phenyl)-5-isoxazolecarboxamide, or 2-{3-[4-(5-Fluoro-2-oxo-2,3-dihydro-1H-benzimidazol-1-yl)-1-piperidinyl]-2-hydroxypropoxy}-N-methylbenzamide, or N-[4-Fluoro-2-({(2S)-3-[4-(5-fluoro-2-oxo-2,3-dihydro-1H-benzimidazol-1-yl)-1-piperidinyl]-2-hydroxypropyl}oxy)phenyl]acetamide trifluoroacetate, or 5-Fluoro-1-(1-{(2S)-2-hydroxy-3-[(2-methyl-1,3-benzoxazol-4-yl)oxy]propyl}-4-piperidinyl)-1,3-dihydro-2H-benzimidazol-2-one trifluoroacetate, or N-[2-({(2S)-3-[4-(5-Fluoro-2-oxo-2,3-dihydro-1H-benzimidazol-1-yl)-1-piperidinyl]-2-hydroxypropyl}oxy)-4-methoxyphenyl]acetamide, or 2-{3-[4-(5-Fluoro-2-oxo-2,3-dihydro-benzoimidazol-1-yl)piperidin-1-yl]-2-hydroxy-propoxy}-N-cyclopropyl-benzamide, or 2-{3-[4-(5-Fluoro-2-oxo-2,3-dihydro-benzoimidazol-1-yl)piperidin-1-yl]-2-hydroxy-propoxy}-N-(3-hydroxypyridin-2-yl)-benzamide, or N-[2-({(2S)-3-[4-(5-Chloro-2-oxo-2,3-dihydro-1H-benzimidazol-1-yl)-1-piperidinyl]-2-hydroxypropyl}oxy)phenyl]acetamide(trifluoroacetate), or 2-({(2S)-3-[4-(5-Chloro-2-oxo-2,3-dihydro-1H-benzimidazol-1-yl)-1-piperidinyl]-2-hydroxypropyl}-N-cyclopropylbenzamide(trifluoroacetate), or N-2-{3-[4-(5-Chloro-2-oxo-2,3-dihydro-benzoimidazol-1-yl)piperidin-1-yl]-2-hydroxy-propoxy}-4-fluorophenyl)-acetamide, or N-(5-Chloro-2-{3-[4-(5-fluoro-2-oxo-2,3-dihydro-benzoimidazol-1-yl)piperidin-1-yl]-2-hydroxy-propoxy}-phenyl)-acetamide, or 5-Fluoro-1-(1-{(2S)-2-hydroxy-3-[(2-methyl-1H-indol-7-yl)oxy]propyl}-4-piperidinyl)-1,3-dihydro-2H-benzimidazol-2-one, or 5-Fluoro-1-(1-{(2S)-2-hydroxy-3-[(6-methoxy-2-methyl-1,3-benzoxazol-4-yl)oxy]propyl}-4-piperidinyl)-1,3-dihydro-2H-benzimidazol-2-one trifluoroacetate, or 5-Fluoro-1-(1-{(2S)-2-hydroxy-3-[(6-hydroxy-2-methyl-1,3-benzoxazol-4-yl)oxy]propyl}-4-piperidinyl)-1,3-dihydro-2H-benzimidazol-2-one trifluoroacetate, or N-[5-Bromo-2-({(2S)-3-[4-(5-fluoro-2-oxo-2,3-dihydro-1H-benzimidazol-1-yl)-1-piperidinyl]-2-hydroxypropyl}oxy)-4-methoxyphenyl]acetamide, or N-Cyclopropyl-4-fluoro-2-({(2S)-3-[4-(5-fluoro-2-oxo-2,3-dihydro-1H-benzimidazol-1-yl)-1-piperidinyl]-2-hydroxypropyl}oxy)benzamide trifluoroaceate, or N-[2-({(2S)-3-[4-(5-Fluoro-2-oxo-2,3-dihydro-1H-benzimidazol-1-yl)-1-piperidinyl]-2-hydroxypropyl}oxy)-4-hydroxyphenyl]acetamide, or N-[5-Bromo-2-({(2S)-3-[4-(5-fluoro-2-oxo-2,3-dihydro-1H-benzimidazol-1-yl)-1-piperidinyl]-2-hydroxypropyl}oxy)-4-hydroxyphenyl]acetamide, or N-[4,5-Difluoro-2-({(2S)-3-[4-(5-fluoro-2-oxo-2,3-dihydro-1H-benzimidazol-1-yl)-1-piperidinyl]-2-hydroxypropyl}oxy)phenyl]acetamide, or N-[5-Fluoro-2-({(2S)-3-[4-(5-fluoro-2-oxo-2,3-dihydro-1H-benzimidazol-1-yl)-1-piperidinyl]-2-hydroxypropyl}oxy)phenyl]acetamide.

22. A process for the preparation of a compound of formula (I) as defined in claim 15 which comprises, (a) reacting a compound of formula

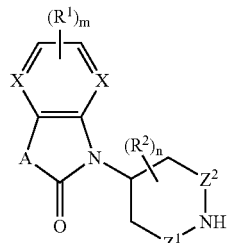

(II)

wherein A, X, m, $R^1$, n, $R^2$, $Z^1$ and $Z^2$ are as defined in formula (I), with a compound of formula

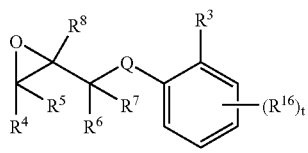

(III)

wherein Q, $R^3$, $R^4$, $R^5$, $R^6$, $R^7$, $R^8$, t and $R^{16}$ are as defined in formula (I); or (b) reacting a compound of formula

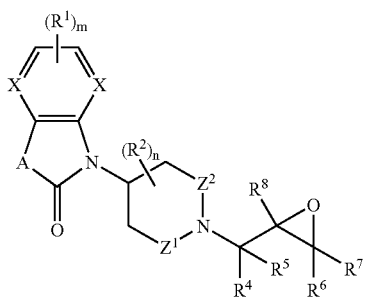

(IV)

wherein A, X, m, $R^1$, n, $R^2$, $Z^1$, $Z^2$, $R^4$, $R^5$, $R^6$, $R^7$ and $R^8$ are as defined in formula (I); with a compound of formula

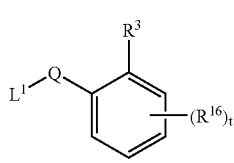

(V)

wherein $L^1$ represents a hydrogen atom or an activating group and Q, $R^3$, t and $R^{16}$ are as defined in formula (I); or (c) when $R^3$ represents —NHC(O)$R^{13}$, reacting a compound of formula

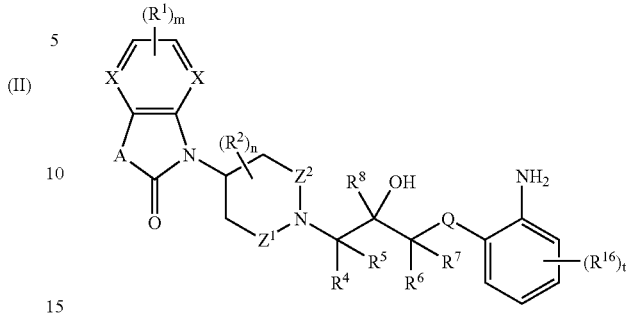

(VI)

wherein A, X, m, $R^1$, n, $R^2$, $Z^1$, $Z^2$, $R^4$, $R^5$, $R^6$, $R^7$, $R^8$, Q, t and $R^{16}$ are as defined in formula (I) with a compound of formula

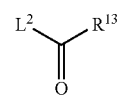

(VII)

wherein $L^2$ represents a leaving group and $R^{13}$ is as defined in formula (I); or (d) when $R^3$ represents —C(O)N$R^{14}R^{15}$, reacting a compound of formula

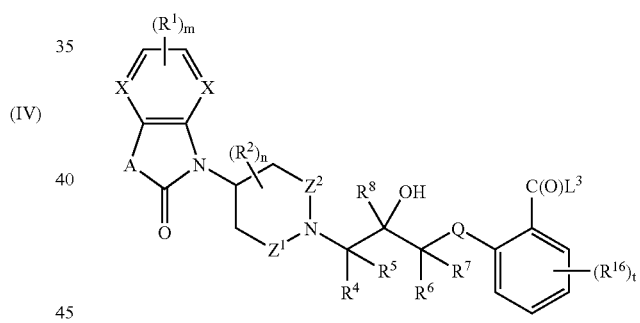

(VIII)

wherein $L^3$ represents a leaving group and A, X, m, $R^1$, n, $R^2$, $Z^1$, $Z^2$, $R^4$, $R^5$, $R^6$, $R^7$, $R^8$, Q, t and $R^{16}$ are as defined in formula (I), with a compound of formula (IX), NH$R^{14}R^{15}$, wherein $R^{14}$ and $R^{15}$ are as defined in formula (I);

and optionally after (a), (b), (c) or (d) forming a pharmaceutically acceptable salt.

23. A pharmaceutical composition comprising a compound of formula (I), or a pharmaceutically acceptable salt, as claimed in claim 15 in association with a pharmaceutically acceptable adjuvant, diluent or carrier.

24. A process for the preparation of a pharmaceutical composition as claimed in claim 23 which comprises mixing a compound of formula (I), or a pharmaceutically acceptable salt, as claimed in claim 15 with a pharmaceutically acceptable adjuvant, diluent or carrier.

25. A process for the preparation of a pharmaceutical composition which comprises mixing a pharmaceutically acceptable salt, as claimed in claim 21 with a pharmaceutically acceptable adjuvant, diluent or carrier.

* * * * *

UNITED STATES PATENT AND TRADEMARK OFFICE
CERTIFICATE OF CORRECTION

PATENT NO. : 7,388,020 B2  Page 1 of 1
APPLICATION NO. : 10/472412
DATED : June 17, 2008
INVENTOR(S) : Tomas Eriksson, Svetlana Ivanova and Hans Lönn It is certified that error appears in the above-identified patent and that said Letters Patent is hereby corrected as shown below:

First Page, Column 2
Under Other Publications, delete "3-aminopropoxyayl" insert -- 3-aminopropoxyaryl --

Column 36
Line 34, delete "trifluoroaceate." insert -- trifluoroacetate. --

Column 41
Line 16, delete "comprising"

Column 42
Line 53, delete "trifluoroaceate," insert -- trifluoroacetate, --

Column 43
Line 52, delete ";" insert -- , --

Column 44
Line 17, after "formula (I)" insert -- , --.

Signed and Sealed this

Nineteenth Day of August, 2008

JON W. DUDAS
*Director of the United States Patent and Trademark Office*